United States Patent

Kawachi et al.

[11] Patent Number: 6,139,801
[45] Date of Patent: Oct. 31, 2000

[54] GAS COLLECTING APPARATUS

[75] Inventors: Takeshi Kawachi, Tokorozawa; Masahiro Moriya, Kiyose; Yasue Sato, Chofu, all of Japan

[73] Assignee: Obayashi Corporation, Osaka, Japan

[21] Appl. No.: 09/101,108

[22] PCT Filed: Nov. 12, 1997

[86] PCT No.: PCT/JP97/04118

§ 371 Date: Apr. 5, 1999

§ 102(e) Date: Apr. 5, 1999

[87] PCT Pub. No.: WO98/22794

PCT Pub. Date: May 28, 1998

[30] Foreign Application Priority Data

| Nov. 19, 1996 | [JP] | Japan | 8-308090 |
| Dec. 6, 1996 | [JP] | Japan | 8-327262 |
| Dec. 25, 1996 | [JP] | Japan | 8-345389 |
| Apr. 14, 1997 | [JP] | Japan | 9-096167 |
| Sep. 25, 1997 | [JP] | Japan | 9-260180 |
| Sep. 25, 1997 | [JP] | Japan | 9-260182 |

[51] Int. Cl.$^7$ .................................................. G01N 1/22
[52] U.S. Cl. .......................... 422/88; 422/110; 422/112; 436/181; 73/863.03; 73/864.81
[58] Field of Search .................... 422/83, 88, 110, 422/112; 73/863.03, 864.81; 436/181

[56] References Cited

U.S. PATENT DOCUMENTS

| 3,945,798 | 3/1976 | Young . | |
| 4,324,146 | 4/1982 | Born | 73/863.12 |
| 4,511,658 | 4/1985 | Lambert et al. . | |
| 4,844,867 | 7/1989 | Bäther . | |
| 5,246,668 | 9/1993 | MacCallum et al. | 422/93 |
| 5,846,831 | 12/1998 | Silvis | 436/55 |
| 5,976,467 | 11/1999 | Dallas et al. | 422/86 |
| 6,037,184 | 3/2000 | Matilainen et al. | 436/177 |

FOREIGN PATENT DOCUMENTS

| 0 142 356 B1 | 8/1988 | European Pat. Off. . |
| 50-62694 | 5/1975 | Japan . |
| 50-118785 | 9/1975 | Japan . |
| 54-36791 | 3/1979 | Japan . |
| 60-170756 | 9/1985 | Japan . |
| 63-221235 | 9/1988 | Japan . |
| 64-33063 | 3/1989 | Japan . |
| 64-53944 | 4/1989 | Japan . |
| 4-51648 | 4/1992 | Japan . |
| 5-26789 | 2/1993 | Japan . |
| 6-43144 | 2/1994 | Japan . |
| 6-117977 | 4/1994 | Japan . |
| 6-174705 | 6/1994 | Japan . |
| 6-221970 | 8/1994 | Japan . |
| WO 88/01299 | 2/1988 | WIPO . |
| WO 90/0737 | 1/1990 | WIPO . |

OTHER PUBLICATIONS

JIS, K 0303, pp:541–5; "Methods for determination of formaldehyde in flue gas" (1993).

*Primary Examiner*—Jeffrey Snay
*Attorney, Agent, or Firm*—Morrison & Foerster, LLP

[57] ABSTRACT

The present invention relates to a gas collecting system collecting an inspection objective gas, such as a toxic gas discharged into an ambient air, and particularly to a gas collecting system which can achieve down-sizing of the system and permit implementation of analysis of gas concentration of the inspection objective gas at high precision with simple operation.

55 Claims, 13 Drawing Sheets

UPON
← GAS COLLECTION
◄---- UPON DISCHARGE

GAS COLLECTING APPARATUS

TECHNICAL FIELD

The present invention relates to a gas collecting system or collecting an inspection objective gas, such as toxic gas or the like, discharged into ambient air, and analyzing concentration of the collected inspection objective gas. More specifically, the invention relates to a gas collecting system which can implement an analysis of gas concentration of an inspection objective gas at high precision with simple operation with achieving downsizing of the system.

BACKGROUND ART

In the recent years, in dwelling houses or so forth employing various newly developed building materials, such as laminated plywood and the like, it has been pointed out that toxic gas of volatile organic compound, such as formic aldehyde and the like, discharged from the newly developed building materials, and such gas should have harmful influence on a living environment. On the other hand, ammonia gas generated from a concrete or paint may promote degradation of exhibits in art museums and museums, or may be a cause of generation of faulty products in a clean room, such as semiconductor manufacturing factories and so forth. Therefore, demand for collection of the toxic gas in the ambient air and analysis of gas concentration, is getting stronger. For providing a measure for such problem of toxic gas, it has been quite important to measure a concentration of toxic gas component in the ambient air, to investigation of a gas generation source and to know a discharge speed of the gas.

As a method for collecting an inspection objective gas, such as toxic gas or the like, a method to condensingly collect a fine amount of gas has been employed, in which a gas collecting system is constructed with a collecting vessel filled with a collecting liquid, an air pump, a drying agent, a flowmeter, a volume flowmeter (integrating flowmeter) and so forth. In an inspection site, an ambient air is introduced into the collecting liquid with measuring a suction amount to continuously cause bubbling by the ambient air in the collecting liquid to dissolve the inspection objective gas in the ambient air into the solution for condensing collection. Then, by analysis of the collecting liquid by a chemical method to dissolve a gas component in the solution is derived to convert into a concentration in the sucked ambient air.

On the other hand, by JIS (Japanese Industrial Standard) A 5908 "particle board", there has been defined a method for measuring a discharge amount of formic aldehyde discharged from a wooden building materials. The method is to introduce a material to be inspected with cutting into a narrow paper tablet like piece into a glass desciccator together with distilled water contained in a tray, to leave for a predetermined period to naturally dissolve formic aldehyde into the distilled water for collection.

However, in the former gas collecting system, it becomes necessary to appropriately control a gas flow rate (flow velocity) for making a gas collection rate constant to read variation of indicia of a gas volumeter with measuring a period by a stop watch, or to frequently adjust a flow velocity by a needle valve with connecting an instantaneous flowmeter. Therefore, in the conventional gas collecting system, it is significantly troublesome for adjustment of flow rate or reading of a gas suction amount. In conjunction therewith, the gas volumeter is precision mechanical equipment, and thus is required sufficient attention in handling for expensiveness and sufficient level of skill. Also, an equipment and material for collection becomes large scale to cause difficulty in transportation of the equipment and material and in movement among inspection sites to make it troublesome for installation and adjustment to make gas collecting operation cumbersome.

On the other hand, in the later method, by inspecting the distilled water, in which formic aldehyde is collected, a gas discharge amount per a unit period can be predicted. However, in this method, it is required to cut a testing piece from the material to be inspected. Therefore, it is not possible to perform inspection for the building completely constructed to limit range of application.

DISCLOSURE OF INVENTION

It is an object of the present invention to provide a gas collecting system which can implement analysis of gas concentration of an inspection objective gas at high precision with simple operation, with achieving downsizing of the system.

A gas collecting system, according to the present invention, comprises a portable air pump which is driven by a portable battery to suck a gas in an inspection objective space, a collection vessel, in which a collecting liquid for collecting an inspection objective gas from the gas is filled, an induction passage having one end connected to the collection vessel and the other end communicated with the inspection objective space for introducing the gas into the collection vessel, a suction passage having one end connected to the collection vessel and the other end connected to a suction port of the air pump for introducing the gas in the collection vessel into the air pump, an accumulation body connected to a discharge port of the air pump, accumulating the gas discharged from the air pump and serving as a volumeter, drying means disposed between the accumulation body and the collection vessel for drying the gas, a pressure switch detecting an internal pressure of the accumulation body, a bypass passage connecting the accumulation body to the suction port of the air pump bypassing the collection vessel, and switching means for switching a flow path connecting the accumulation body to either one of the discharge port of the air pump and the bypass passage, and in conjunction therewith, connecting the discharge port of the air pump to an ambient air opening passage when the accumulation body is connected to the bypass passage.

On the other hand, the system includes a main receptacle box and an auxiliary receptacle box mounted on the main receptacle box, the main receptacle box receives the air pump and the battery therein and has mounting surfaces for mounting the drying means and the collection vessel, the auxiliary receptacle box receives the switching means and the pressure switch therein, and has a mounting portion for detachably mounting the accumulation body.

The accumulation body is a foldable and exchangeable bag.

The bag is a vinyl bag.

The collection vessel is formed with transparent material to be used as a color comparison tube, and is also used as a reaction tube to be filled with reagents reacting with the inspection objective gas.

The pressure switch detects an internal pressure of the accumulation body reaching a predetermined pressure to output a stop signal for the air pump.

The pressure switch is connected among the air pump, a buzzer and a power source supplying operation power to the air pump and the buzzer, the pressure switch being constructed with a bag-formed extending member communicated with the accumulation body and causing expanding and contracting deformation by a pressure of the gas introduced from the accumulation body, a cylindrical guide surrounding the extending member to guide the extending member in expanding direction, and a switch main body being provided in opposition to the extending member in expanding direction thereof and being depressed by the expanding member for selectively establishing connection between a common terminal and either one of two switching terminals, wherein, each of the switching terminals is connected to the buzzer and the air pump, respectively, and the common terminal is connected to the power source, and when an internal pressure of the accumulation body is reached to a predetermined pressure, the connection with the common terminal is switched from the switching terminal of the air pump to the switching terminal of the buzzer by the extending member expanded in response thereto.

At least one of the induction passage and the suction passage has a capillary portion.

The collection vessel is formed into a cylindrical shape and its opening portion is closed by a cap, and the induction passage and the suction passage has an injection needle form tube portion, respectively, these tube portions being inserted into the collection vessel through the cap.

At least a portion of the cap covering the opening portion of the collection vessel is coated with an insulation layer of a material not influencing the collecting liquid.

The injection needle form tube portion is closed at a tip end thereof and is formed with a laterally oriented communication opening in the vicinity of the tip end portion.

The switching means is connected to a speed adjusting switch controlling driving speed of the air pump by varying a supply voltage to the air pump from the battery in response to switching operation of the flow path, when the discharge port of the air pump is connected to the accumulation body, the air pump is driven at low speed, and when the bypass passage is connected to the accumulation body, the air pump is driven at high speed.

A check valve is provided on the upstream side of the suction port of the air pump to only allow the gas flow to the suction port.

A given amount of 2N-NaOH solution as the collecting liquid is filled in the collection vessel, after passing a given amount of the gas containing the inspection objective gas, a given amount of AHMT reagent prepared by using $HClO_4$ as the reagents is filled within the collection vessel to leave for a given period, and in conjunction with, an indication value is adjusted to a predetermined value by setting a standard color solution in an absorptiometer, then, a given amount of $KIO_4$ reagent as said reagents is added into the collection vessel, and then, the collection vessel is set in the absorptiometer for detecting concentration of formic aldehyde from the indication value thereof.

A given amount of 2N-KOH solution as the collecting liquid is filled in the collection vessel, after passing a given amount of the gas containing the inspection objective gas, a given amount of AHMT reagent as the reagents is filled within the collection vessel to leave for a given period, and in conjunction with, an indication value is adjusted to a predetermined value by setting a standard color solution in an absorptiometer, then, a given amount of $KIO_4$ reagent as the reagents is added into the collection vessel, and then the collection vessel is set in the absorptiometer for detecting concentration of formic aldehyde from the indication value thereof.

On the other hand, a gas collecting system, according to the present invention, comprises a portable air pump which is driven by a portable battery to suck a gas in an inspection objective space, a collection vessel, in which a collecting liquid for collecting an inspection objective gas from the gas is filled, an induction passage having one end connected to the collection vessel and the other end communicated with the inspection objective space for introducing the gas into the collection vessel, a suction passage having one end connected to the collection vessel and the other end connected to a suction port of the air pump for introducing the gas in the collection vessel into the air pump, an accumulation body connected to a discharge port of the air pump, accumulating the gas discharged from the air pump and serving as a volumeter, drying means disposed between the accumulation body and the collection vessel for drying the gas, a pressure switch detecting an internal pressure of the accumulation body, a bypass passage connecting the accumulation body to the suction port of the air pump bypassing the collection vessel, switching means for switching a flow path connecting the accumulation body to either one of the discharge port of the air pump and the bypass passage, and in conjunction therewith, connecting the discharge port of the air pump to an ambient air opening passage when the accumulation body is connected to the bypass passage, a main receptacle box receiving the air pump and the battery therein and having mounting surfaces for mounting the drying means and the collection vessel, and an auxiliary receptacle box mounted on the main receptacle box, receiving the switching means and the pressure switch therein, and having a mounting portion for detachably mounting the accumulation body, wherein, the collection vessel is formed of a transparent material to be used as a color comparison tube, and is also used as a reaction tube filled with reagents reacting with the inspection objective gas, the pressure switch detects an internal pressure of the accumulation body reaching a predetermined pressure for outputting a stop signal of the air pump, and the accumulation body is a foldable and exchangeable bag.

In the gas collecting system according to the present invention constructed as set forth above, mainly, the gas in the inspection objective space is taken into the collection vessel by driving the air pump to pass the gas through the collection liquid of the collection vessel. Thereafter, the gas is sucked into the air pump through the drying means, and the gas discharged from the air pump is accumulated in the accumulation body to permit the accumulation body as volumeter.

On the other hand, for the inspection objective gas collected by the collection liquid of the collection vessel, inspection can be performed by using the collection vessel as the reaction tube and the color comparison tube. Therefore, transfer of the collection liquid and dividing of a part of the collection liquid for analysis become unnecessary to improve operability in chemical analysis.

Furthermore, after completion of collection in one time, by varying flow path of the switching means, the gas within the accumulation body is automatically discharged from the ambient air opening passage with sucking by the air pump to enable preparation for next collection after making the accumulation body empty. Accordingly, the gas collecting system can be simplified in construction, significantly, inexpensive and compact, and can be operated easily without requiring skill.

On the other hand, by associating the pressure switch of the accumulation body with the air pump, the air pump can be stopped automatically at a time when the internal pressure of the accumulation body reaches the predetermined pressure. Therefore, collecting operation can be automatically terminated and gas suction management complicates and requiring skill as in the prior art, become unnecessary.

Furthermore, the opening portion of the collection vessel is closed by the cap, the induction passage introducing the gas into the collection vessel and the suction passage introducing the gas into the air pump are formed with the injection needle tube portions with the capillary portions. Since these tube portions are mounted through the cap, setting and exchanging of the collection vessel is quite easy. Also, since the capillary portion of the induction passage can also serve as a resistance tube of the gas flow, stabilization of the gas flow rate can be achieved to enable enhancement of precision in inspection.

On the other hand, since at least the portion of the cap covering the opening portion of the collection vessel is covered with the insulation layer, penetration of gas component generated from the cap into the collection vessel can be prevented by the insulation layer. Therefore, even when the collection liquid is preliminarily filled in the collection vessel, influence of gas component generated by the cap for the collection liquid can be avoided. Therefore, the collection vessel can be stored for a long period in the condition where the collection liquid is preliminarily filled.

Accordingly, upon performing gas analysis by the gas collecting system, analyzing operation can be done easily and quickly only by setting the collection vessel preliminarily filled with the collection liquid. Also, storage ability of the collection vessel filled with the collection liquid can be significantly improved. Therefore, large amount of collection vessels containing the collection liquid can be produced at once. In comparison with the case where the collection vessel and the collection liquid are soled separately, the collection vessel containing the collection liquid can be traded as a product. Furthermore, even when a large amount of collection vessels in which the collection liquid fills system is stocked, a blank value can be stable to improve precision in analysis. Furthermore, since the cap does not affect for the collecting liquid, inexpensive material can be used as the material for the cap.

On the other hand, the pressure switch is disposed between the buzzer and air pump, and the power source to control ON/OFF of actuation of the buzzer and the air pump. When the inside of the accumulation body is filled with a given amount of gas, driving of the air pump is automatically stopped to stop sucking of the gas. Simultaneously, the buzzer is actuated to notice this to permit to construct the gas collecting system to be convenient to use and permit accurate measurement.

Particularly, the pressure switch is designed to selectively connect the common terminal of the switch body with switching terminals by expansion of the extending member introduced the gas pressure. Thus, construction becomes simple to permit downsizing to facilitate assembling of the system to lower cost to permit manufacturing at low cost. On the other hand, since expansion of the extending member can be guided by the guide, detection can be assured even when the gas pressure is small to achieve high performance.

On the other hand, the system may further comprises a casing covering the inspection objective space in a sealing condition from outside to enclose the inspection objective gas discharged from an inspection object enclosed therein, a sampling port provided with the casing, and connected to the induction passage for introducing the gas containing the inspection objective gas in the casing into the collection vessel, a supply port provided with the casing for supplying a reference gas into the casing depending upon suction of the gas in the casing by the air pump, and a capillary passage disposed between the sampling port and the accumulation body for lowering flow velocity of the gas sucked.

The capillary passage is disposed between the sampling port and the collection vessel.

A filter is connected to the supply port, and the reference gas is an ambient air purified by the filter.

A reference gas receptacle body filled with the reference gas is connected to the supply port, and the reference gas is supplied to the casing from the reference gas receptacle body.

Also, a gas collecting system, according to the present invention, comprises a casing covering an inspection objective space in a sealing condition from outside to enclose an inspection objective gas discharged from an inspection object enclosed therein, a sampling port provided with the casing to sample a gas containing the inspection objective gas in the casing, an air pump sucking the gas from the inspection objective space in the casing, a supply port provided with the casing for supplying a reference gas into the casing depending upon suction of the gas in the casing by the air pump, a collection vessel, in which a collection liquid for collecting the inspection objective gas from the gas is filled, an induction passage having one end connected to the collection vessel and the other end connected to the sampling port for introducing the gas into the collection vessel, a suction passage having one end connected to the collection vessel and the other end connected to a suction port of the air pump for introducing the gas in the collection vessel into the air pump, an accumulation body connected to a discharge port of the air pump, accumulating the gas discharged from the air pump and serving as a volumeter, a capillary passage disposed between the sampling port and the accumulation body for lowering flow velocity of the gas sucked, drying means disposed between the accumulation body and the collection vessel for drying the gas;
  a pressure switch detecting an internal pressure of the accumulation body;
  a bypass passage connecting the accumulation body to the suction port of the air pump bypassing the collection vessel; and
  switching means for switching a flow path connecting the accumulation body to either one of the discharge port of the air pump and the bypass passage, and in conjunction therewith, connecting the discharge port of the air pump to an ambient air opening passage when the accumulation body is connected to the bypass passage, wherein, the casing has an opening in a bottom portion, on which a packing for fitting the casing with the inspection object in gas-tight fashion is provided, a filter is connected to the supply port, and the reference gas is an ambient air purified by the filter.

In the gas collecting system according to the present invention constructed as set forth above, by abutting the casing onto the surface of the inspection object, the interior in the casing becomes sealed condition to enclose the inspection objective gas discharged from the inspection object. Then, the inspection objective gas collected within the casing is mixed with the reference gas introduced through the supply port and supplied to the collection vessel through the sampling port. Accordingly, in the collection vessel, detection can be performed by separating the inspection objective gas mixed to the reference gas. Thus, the gas discharge amount per unit period of the inspection object to be inspected can be easily detected.

On the other hand, since the casing is formed the opening in the bottom portion, and the packing is mounted on the peripheral edge of the opening, the interior of the casing can be sealed condition by the packing on the peripheral edge of the opening by fitting the opening of the casing in gas-tight fashion on the inspection object, such as the existing floor, wall and so forth when the inspection object cannot be cut as the test piece, such as the floor, the wall or so forth of the existing building. Therefore,even from the floor and the wall, the inspection objective gas can be sampled. Thus, not only for material inspection before construction, but also for the existing building after construction, the gas discharge amount can be easily measured at arbitrary position. Also, even if the inspection object is constructed by composing different kinds of materials, measurement in the actually constructed condition becomes possible, and inspection of the gas discharge amount per unit area discharged from individual material in the constructed building becomes possible to be useful for study of gas discharge phenomenon.

On the other hand, since the capillary passage is provided in the sampling port to adjust flow velocity of the gas, in which the inspection objective gas is admixed excessive lowering of pressure in the casing when the gas within the casing is sucked through the sampling port. Accordingly, penetration of the ambient air into the casing through the peripheral edge of the opening of the casing can avoided, and in addition, forced discharge of the inspection objective gas from the inspection object by excessively lowering of pressure can be avoided to enhance precision of inspection.

Also, the system may further comprises a casing covering the inspection objective space in a sealing condition from outside to enclose the inspection objective gas discharged from an inspection object enclosed therein, a sampling port provided with the casing, and connected to the induction passage for introducing the gas containing the inspection objective gas in the casing into the collection vessel, an internal pressure maintaining bag provided in the casing and having expandability and sealing ability, and a pressure induction passage connected to the internal pressure maintaining bag through the casing and introducing a pressure adjusting gas for expanding the internal pressure maintaining bag according to lowering of the internal pressure of the casing.

The casing has an opening in a bottom portion, and a packing for fitting the casing with the inspection object in gas-tight fashion is provided on the opening.

The casing is a chamber receiving a material piece to be inspected as the inspection object.

The casing is formed of a transparent material.

A stirring means is provided in the casing and the stirring means stirs the gas in the casing.

The pressure adjusting gas is introduced through the pressure induction passage into the internal pressure maintaining bag by a pressure reduction in the casing.

A port opening and closing means is disposed between the sampling port and the induction passage for opening and closing therebetween, and a pressure introducing means for opening and closing the pressure introducing passage is provided therewith.

Furthermore, the system may includes a volume varying bag provided in the casing and having expandability and sealing ability, and a gas supplying and discharging passage connected to the volume varying bag through the casing, for supplying and discharging a volume adjusting gas to the volume varying bag to vary volume in the casing by expanding and deflating the volume varying bag.

At least either one of the internal pressure maintaining bag and the volume varying bag is disposed in plural in the casing.

An opening and closing means for the gas supplying and discharging passage is provided therewith.

An adjusting gas receptacle body filled with the pressure adjusting gas or the volume adjusting gas is connected to at least either one of the pressure induction passage and the gas supplying and discharging passage, and these gas are supplied from the adjusting gas receptacle body.

Furthermore, a gas collecting system, according to the present invention, comprises a casing covering an inspection objective space in a sealing condition from outside to enclose an inspection objective gas discharged from an inspection object enclosed therein, a sampling port provided with the casing to sample a gas containing the inspection objective gas in the casing, an air pump sucking the gas from the inspection objective space in the casing, a collection vessel filled with a collecting liquid for collecting the inspection objective gas from the gas, an induction passage having one end connected to the collection vessel and the other end connected to the sampling port for introducing the gas into the collection vessel, a suction passage having one end connected to the collection vessel and the other end connected to a suction port of the air pump for introducing the gas in the collection vessel into the air pump, an accumulation body connected to a discharge port of the air pump, accumulating the gas discharged from the air pump and serving as a volumeter, drying means disposed between the accumulation body and the collection vessel for drying the gas, a pressure switch detecting an internal pressure of the accumulation body, a bypass passage connecting the accumulation body to the suction port of the air pump bypassing the collection vessel, switching means for switching a flow path connecting the accumulation body to either one of the discharge port of the air pump and the bypass passage, and in conjunction therewith, connecting the discharge port of the air pump to an ambient air opening passage when the accumulation body is connected to the bypass passage, an internal pressure maintaining bag provided in the casing and having expandability and sealing ability, a pressure induction passage connected to the internal pressure maintaining bag through the casing and introducing a pressure adjusting gas for expanding the internal pressure maintaining bag according to lowering of the internal pressure of the casing, a volume varying bag provided in the casing and having expandability and sealing ability, and a gas supplying and discharging passage connected to the volume varying bag through the casing, for supplying and discharging a volume adjusting gas to the volume varying bag for varying volume in the casing by expanding and deflecting the volume varying bag.

In the gas collecting system according to the present invention constructed as set forth above, the expandable internal pressure maintaining bag in the casing covering the inspection object in the sealed condition is provided to make it possible to introduce the pressure adjusting gas within the internal pressure maintaining bag. Therefore, when a given amount of gas is sampled within the casing for measuring concentration of the inspection objective gas, the pressure in the casing in the sealed condition can be lowered depending upon the sampling amount. However, since the pressure adjusting gas is introduced into the pressure maintaining bag in a volume corresponding to the sampling amount due to pressure reduction effect, to cause expansion to maintain the gas pressure within the casing constant.

On the other hand, by the internal pressure maintaining bag having sealing ability, the pressure adjusting gas is not mixed with the gas containing the inspection objective gas within the casing and thus, the inspection objective gas to be sampled may not be diluted. Accordingly, by making the concentration of the inspection objective gas higher, the precision of inspection can be improved.

On the other hand, since the lowering of the pressure within the casing can be avoided, the gas generation amount from the inspection object may not be increased by the pressure reducing effect, and the casing is not required high pressure resistive sealing ability.

Also, since the volume varying bag is provided in addition to the foregoing internal pressure maintaining bag, the net volume of the casing can be varied without providing many kinds of casing of different volumes by preliminarily expanding the volume varying bag within the casing. Therefore, when the released amount of the inspection objective gas from the inspection object is small and gas concentration in the casing cannot reach the concentration, at which measurement is possible unless leaving for a long period, high concentration of the gas can be established within a short period even when gas discharge amount is small by adjusting the net volume of the casing smaller by expanding the volume variable bag. Also, even when the gas is sampled from the casing of the reduced net volume, the internal pressure maintaining bag on the other hand is expanded following to taking out of the gas from the casing to permit to maintain the gas pressure within the casing constant.

Furthermore, a gas collecting system, according to the present invention, comprises a casing covering an inspection objective space in a sealing condition from outside to enclose an inspection objective gas discharged from an inspection object enclosed therein, a pair of gas circulating ports provided with the casing and circulating a gas through the casing, an air pump sucking the gas containing the inspection objective gas from the inspection objective space in the casing, a collection vessel, in which a collection liquid collecting the inspection objective gas from the gas is filled, an induction passage having one end connected to the collection vessel and the other end connected to one of the gas circulating ports of the casing for introducing the gas into the collection vessel, a suction passage having one end connected to the collection vessel and the other end connected to a suction port of the air pump for introducing the gas in the collection vessel into the air pump, a buffer disposed between a discharge port of the air pump and the other of the gas circulating ports of the casing to buffer a gas pressure by temporarily storing the gas discharged from the air pump, and in conjunction therewith, to circulate the gas to the casing again, and humidity adjusting means disposed between the buffer and the collection vessel for adjusting a humidity of the gas circulated to be constant.

The casing has an opening in a bottom portion, and a packing for fitting the casing with the inspection object in gas-tight fashion is provided on the opening.

The casing is a chamber receiving a material piece to be inspected as the inspection object.

The casing is formed of a transparent material.

The buffer is a bag to be expanded and deflected depending upon a difference between a pressure of the gas stored therein and an ambient air pressure.

The humidity adjusting means is a container filled with a humidity adjusting liquid adjusting humidity of the gas.

The humidity adjusting liquid is a salt solution.

The collection vessel is provided in plural and in parallel, and switching device disposed between the collection vessels and one of the gas circulating ports of the casing to selectively communicate the casing with either one of the collection vessels.

The switching device switches the communication between the respective collection vessels and the casing according to an elapsed time.

The switching device is controlled the switching operation by means of a timer.

The air pump is portable and is driven by a portable battery.

The collection vessel is formed with transparent material to be used as a color comparison tube, and is also used as a reaction tube to be filled with reagents reacting with the inspection objective gas.

The collection vessel is formed into a cylindrical shape and its opening portion is closed by a cap, and the induction passage and the suction passage having an injection needle form tube portion, respectively, these tube portions being inserted into the collection vessel through the cap.

The cap is coated with an insulation layer of a material not influencing the collecting liquid at least at a portion covering the opening portion of the collection vessel.

A given amount of 2N-NaOH solution as the collecting liquid is filled in the collection vessel, after passing a given amount of the gas containing the inspection objective gas, a given amount of AHMT reagent prepared by using $HClO_4$ as the reagents is filled within the collection vessel to leave for a given period, and in conjunction therewith, an indication value is adjusted to a predetermined value by setting a standard color solution in an absorptiometer, then, a given amount of $KIO_4$ reagent as the reagents is added into the collection vessel, and then, the collection vessel is set in the absorptiometer for detecting concentration of formic aldehyde from the indication value thereof.

A given amount of 2N-KOH solution as the collecting liquid is filled in the collection vessel, after passing a given amount of the gas containing the inspection objective gas, a given amount of AHMT reagent as the reagents is filled within the collection vessel to leave for a given period, and in conjunction with, an indication value is adjusted to a predetermined value by setting a standard color solution in an absorptiometer, then, a given amount of $KIO_4$ reagent as the reagents is added into the collection vessel, and then, the collection vessel is set in the absorptiometer for detecting concentration of formic aldehyde from the indication value thereof.

On the other hand, a gas collecting system, according to the present invention, comprises a casing covering an inspection objective space in a sealing condition from outside to enclose an inspection objective gas discharged from an inspection object enclosed therein, a pair of gas circulating ports provided with the casing to circulate a gas through the casing, an air pump sucking the gas containing the inspection objective gas from the inspection objective space in the casing, a collection vessel filled with a collection liquid for collecting the inspection objective gas from the gas, an induction passage having one end connected to the collection vessel and the other end connected to one of the gas circulating ports of the casing for introducing the gas into the collection vessel, a suction passage having one end connected to the collection vessel and the other end connected to a suction port of the air pump for introducing the gas in the collection vessel into the air pump, a buffer disposed between a discharge port of the air pump and the other of the gas circulating ports of the casing to buffer a gas pressure by temporarily storing the gas discharged from the air pump, and in conjunction therewith, to supply the gas to the casing again, and humidity adjusting means disposed between the buffer and the collection vessel for adjusting a humidity of the gas circulated to be constant, wherein, the casing has an opening in a bottom portion, on which a packing for fitting the casing with the inspection object in gas-tight fashion is provided, the collection vessel is formed with transparent material to be used as a color comparison tube, and is also used as a reaction tube to be filled with reagents reacting with the inspection objective gas, the buffer is a bag to be expanded and deflected depending upon a difference between a pressure of the gas stored therein and an ambient air pressure, and the humidity adjusting means is a container filled with a humidity adjusting liquid prepared by a salt solution for adjusting humidity of the gas.

Furthermore, a gas collecting system, according to the present invention, also comprises a casing covering an inspection objective space in a sealing condition from outside to enclose an inspection objective gas discharged from an inspection object enclosed therein, a pair of gas circulating ports provided with the casing and circulating a gas through the casing, an air pump sucking the gas containing the inspection objective gas from the inspection objective space in the casing, a collection vessel filled with a collection liquid collecting the inspection objective gas from the gas, an induction passage having one end connected to the collection vessel and the other end connected to one of the gas circulating ports of the casing for introducing the gas into the collection vessel, a suction passage having one end connected to the collection vessel and the other end connected to a suction port of the air pump for introducing the gas in the collection vessel into the air pump, a buffer disposed between a discharge port of the air pump and the other of the gas circulating ports of the casing to buffer a gas pressure by temporarily storing the gas discharged from the air pump, and in conjunction therewith, to circulate the gas to the casing again, and humidity adjusting means disposed between the buffer and the collection vessel for adjusting a humidity of the gas circulated to be constant, wherein the casing has an opening in a bottom portion, on which a packing for fitting the casing with the inspection object in gas-tight fashion is provided, the buffer is a bag to be expanded and deflected depending upon a difference between a pressure of the gas stored therein and an ambient air pressure, the humidity adjusting means is a container filled with a humidity adjusting liquid prepared by a salt solution for adjusting humidity of said gas, the collection vessel is provided in plural and in parallel, the collection vessels being formed with transparent material to be used as a color comparison tube, and being also used as a reaction tube to be filled with reagents reacting with the inspection objective gas, and switching device is disposed between the collection vessels and one of the gas circulating ports of the casing to selectively communicate the casing with either one of the collection vessels according to time counted.

In the gas collecting system according to the present invention constructed as set forth above, by simply fitting the casing on the inspection object and driving the air pump, the gas is circulated through the casing. In conjunction therewith, the inspection objective gas collected within the enclosed casing is taken into the collection vessel. The gas is sucked from the collection vessel and accumulated within the buffer. The gas again returned into the casing is purified as the inspection objective gas is collected in the collection vessel and the humidity thereof is maintained constant by the humidity adjusting means. After performing collection of the inspection objective gas by circulating the gas within the closed loop circuit for a predetermined period, the quantitative analysis of the inspection objective gas may be performed by the collection vessel. Thus, the inspection objective gas can be collected without damaging the inspection object. By this, not only inspection for the construction material as independent material but also at the arbitrary position in the use condition of the material, namely in the building after construction, the inspection objective gas can be sampled to permit inspection of the material. At this time, adjustment or so forth of the system upon collection is unnecessary to simplify handing to require no skill. Also, the gas collecting operation and gas measurement can be performed at arbitrary position to be inspected.

Also, since the gas can be circulated within the closed loop without causing variation of pressure by the buffer, error in measurement can be avoided with simple construction.

On the other hand, by providing a plurality of collection vessels and switching connection of the collection vessels with the casing per preliminarily set collection period, gas collection according to time counted becomes possible to monitor variation of the discharge amount of the inspection objective gas according to the elapsed time.

BEST MODE FOR CARRYING OUT OF THE INVENTION

Figure 1:
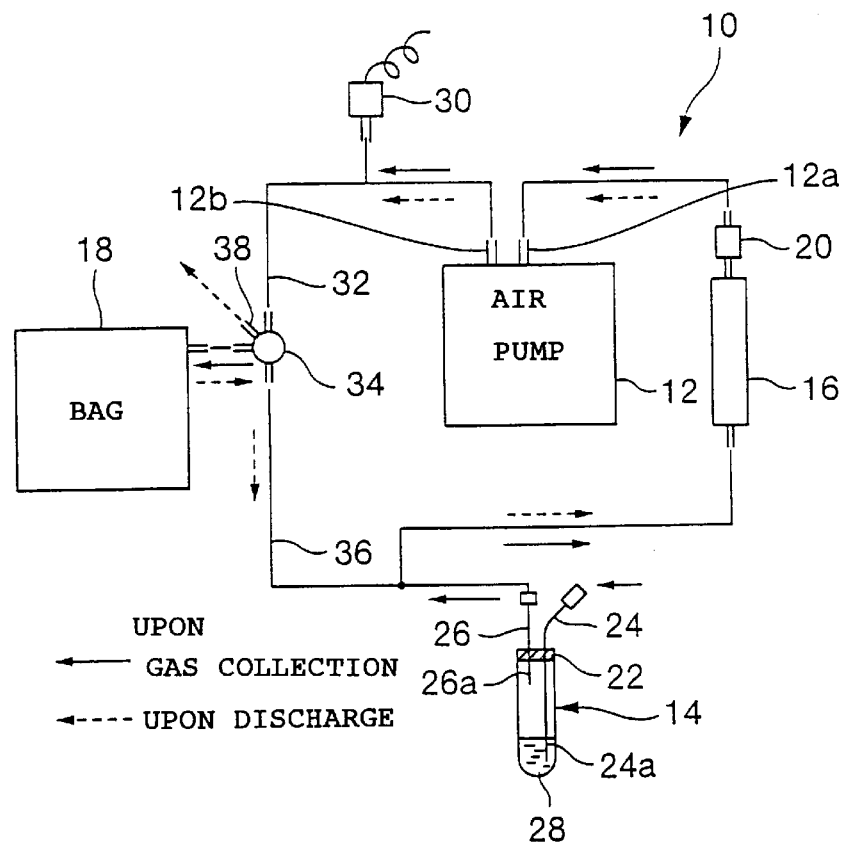
FIG. 1 is a circuit diagram of an entire circuit of the first embodiment of a gas collecting system according to the present invention.

The preferred embodiments of the present invention will be discussed hereinafter in detail with reference to the accompanying drawings.

The first embodiment of a gas collecting system according to the present invention basically includes a portable air pump 12 which is driven by a portable battery to suck a gas in an inspection objective space, an impinger 14 as a collecting vessel, in which a collecting liquid 28 for collecting an inspection objective gas from the foregoing gas is filled, a tube 24 having one end connected to the impinger 14 and the other end communicated with the foregoing inspection objective space for serving as an induction flow passage for introducing the foregoing gas into the impinger 14, a tube 26 having one end connected to the foregoing impinger 14 and the other end connected to a suction port 12a of the foregoing air pump 12 for serving as a suction flow passage introducing the foregoing gas into the air pump 12, a bag 18 connected to a discharge port 12b of the air pump 12 and accumulating the foregoing gas discharged from the air pump 12 for serving as a storage body operating as a volumeter, a drying agent tube 16 disposed between the bag 18 and the impinger 14 and serving as drying means for drying the foregoing gas, a pressure switch 30 detecting an internal pressure of the foregoing bag 18, a tube 36 as a bypass passage connecting the foregoing bag 18 to the foregoing suction port 12a of the foregoing air pump 12 bypassing the foregoing impinger 14, a switching cock 34 serving as switching means for switching a flow passage connecting the foregoing bag 18 to either one of the foregoing discharge port 12b and the foregoing tube 36, and, in conjunction therewith, connecting the discharge port 12b of the air pump 12 to an ambient air communication passage 38 when the bag 18 is connected to the tube 36, a main receptacle box 40 receiving the foregoing air pump 12 and the foregoing battery therein, and in conjunction therewith, having mounting surfaces 40a and 40b on the outer surface for mounting the foregoing drying agent tube 16 and the foregoing impinger 14, and an auxiliary receptacle box 42 mounted on the main receptacle box 40, receiving the foregoing switching cock 34 and the foregoing pressure switch 30 therein and having a mounting portion 46 for detachably mounting the foregoing bag 18. The impinger 14 is formed of a transparent material and to be used as a color comparison tube, and also as a reaction tube to be filled reagents reacting with the inspection objective gas. On the other hand, the pressure switch 30 detects the internal pressure of the bag 18 reaching the predetermined pressure to output a stop signal of the air pump 12. Also, the bag 18 is foldable and exchangeable.

Discussing in detail, the shown embodiment of the gas collecting system 10 is a type sucking the ambient air, and includes the portable air pump 12 as shown in FIG. 1. By sucking the ambient air in the inspection objective space with the air pump 12, the inspection objective gas in the ambient air is taken. The foregoing air pump 12 is portable as driven by a not shown portable battery, such as a dry cell or the like. In the suction port 12a of the air pump 12, the impinger 14 and the drying agent tube 16 also used as a filter, are provided in sequential order. Also, in the discharge port 12b of the air pump 12, the bag 18 accumulating the gas discharged from the discharge port 12b is provided. The bag 18 is used as volumeter measuring a gas amount. On the other hand, on the downstream side of the drying agent tube 16, a check valve 20 permitting only flow of gas in a direction toward the suction port 12a of the air pump 12 is provided.

The impinger 14 is formed by a bottomed cylindrical glass tube in a test tube like configuration, in which an opening portion on the upper end is closed by an elastic cap 22. In the impinger 14, the tube 24 for introducing an ambient air and the tube 26 connecting the interior of the impinger 14 to the suction port 12a are provided. These tubes 24 and 26 are formed by metallic capillaries of injection needle form. Then, the tubes 24 and 26 formed by metallic capillaries are pierced into the elastic cap 22 to insert respective needle shaped tip end portions 24a and 26a into the impinger 14. On the other hand, in the impinger 14, a predetermined amount of the collecting liquid 28 is filled. The tip end portion 24a of the tube 24 is dipped into the collecting liquid 28, and in conjunction therewith, the tip end portion 26a of the tube 26 is located above the liquid surface of the collecting liquid 28.

The pressure switch 30 is provided between the air pump 12 and the bag 18. The pressure within the bag 18 is detected by the pressure switch 30. At a timing, at which the bag 18 is filled with the air, the air pump 12 is stopped.

On the other hand, on the downstream side of the pressure switch 30, the switching cock 34 is provided in the discharge tube 32 communicated with the bag 18. The switching cock 34 connects the bag 18 to the discharge tube 32 of the air pump 12 at the normal position shown in FIG. 2(a), and the bag 18 to the tube 36 bypassing the impinger 14 at the switched position shown in FIG. 2(b). At the switched position of the switching cock 34, the discharge pipe 32 is communicated with the ambient air communication passage 38.

Figure 3:
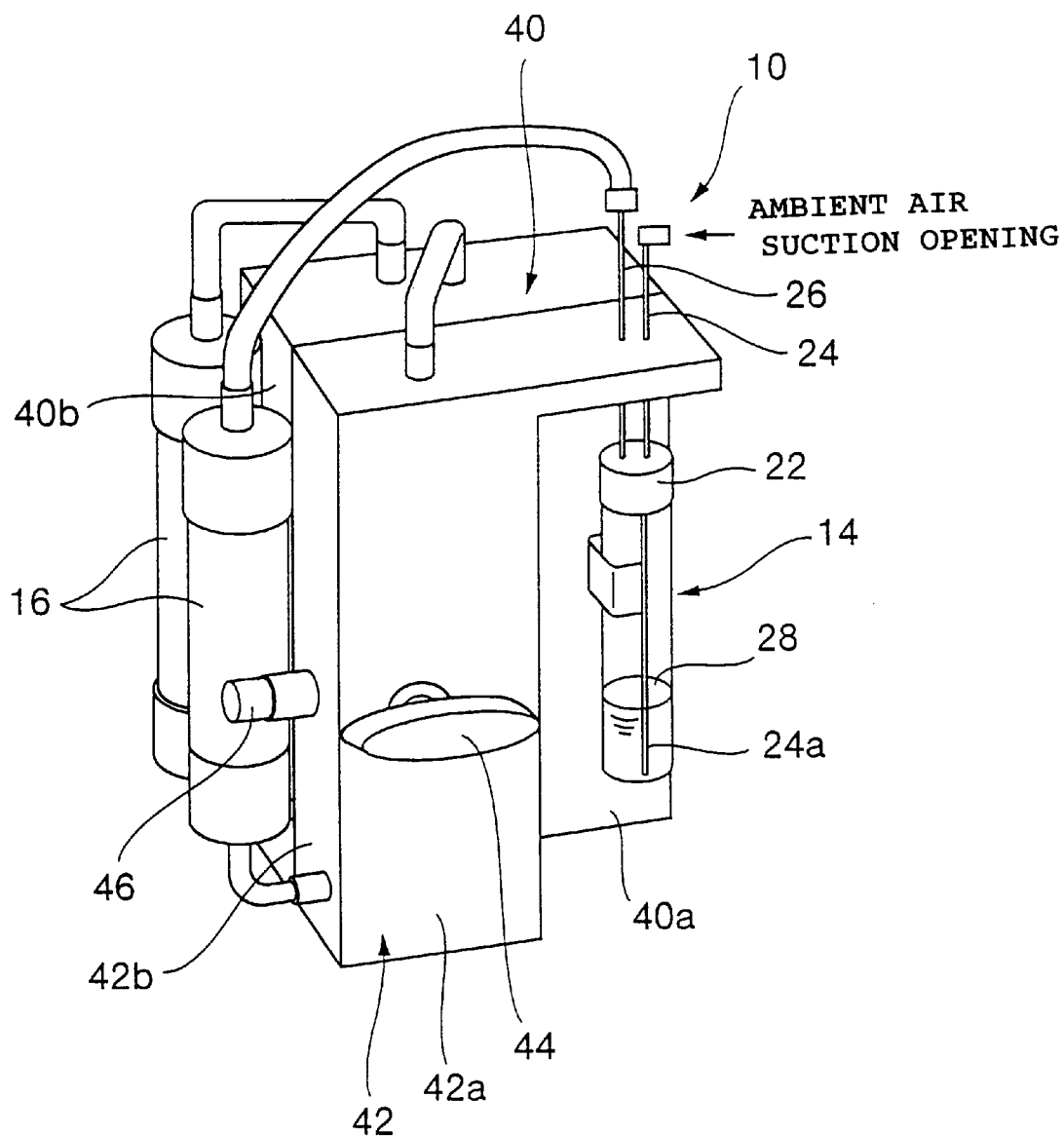
FIG. 3 is a perspective view showing an assembled condition of the gas collecting system shown in FIG. 1.

The gas collecting system 10 constructed as set forth above, is assembled as a compact construction as shown in FIG. 3. Namely, on the side surface 40a on the near side of the main receptacle box 40 receiving the air pump 12 and the dry cell or so forth to be the driving source, the auxiliary receptacle box 42 receiving the switching cock 34, the pressure switch 30 and so forth, is mounted with occupying approximately half of the space. On the side surface 42a on the near side of the auxiliary receptacle box 42, a lever 44 of the switching cock 34 is projected. On the other hand, on the side surface 42b on the side, a mounting portion 46 of the bag 18 is provided. On the other hand, on the side surface 40b on the side of the main receptacle box 40, two drying agent tubes 16 are mounted. Also, on the side surface 40a on the near side of the main receptacle box 40, the impinger 14 is mounted at the position on the side of the auxiliary receptacle box 42. For example, the gas collecting system is formed in a size having 10 cm of depth, 12 cm of width and 18 cm of height.

In the shown embodiment of the gas collecting system 10 constructed as set forth above, by driving the air pump 12, the ambient air in the measuring site is introduced into the impinger 14 through the tube 24 to pass the collecting liquid 28 in the impinger 14 with bubbling the latter, and then sucked into the air pump 12 through the drying agent tube 16. The gas discharged from the air pump 12 is accumulated in the bag 18. Then, by using the bag 18 as the volumeter, the pressure switch 30 is actuated at a timing where the bag is filled to stop the air pump 12 to complete collecting operation of the inspection objective gas. At this timing, the inspection objective gas in the ambient air is admixed with the collecting liquid 28 of the impinger 14 to perform inspection with taking the impinger 14 as the reaction vessel and the color comparison tube.

Figure 2:
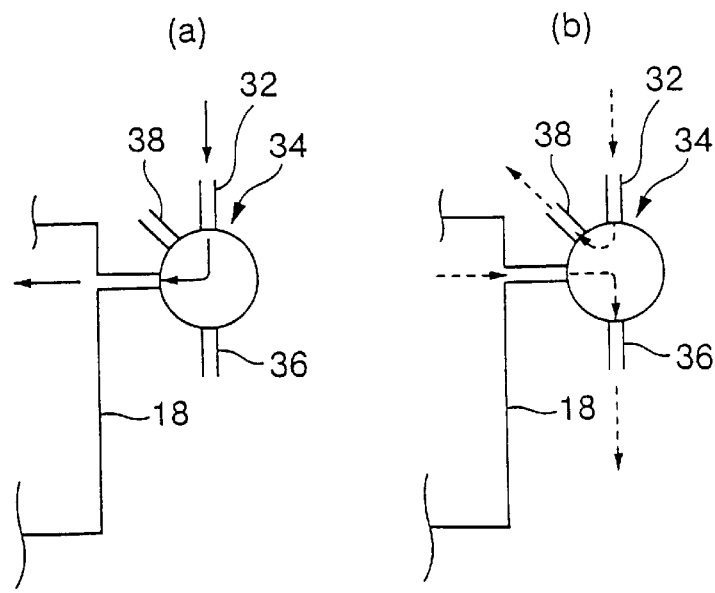
FIG. 2 is an explanatory illustration of a switching cock to be provided in the gas collecting system shown in FIG. 1.

After completion of one cycle of collecting operation, by setting the switching cock 34 at the switched position shown in FIG. 2(b), the bag 18 is connected to the suction port 12a of the air pump 12 so that the gas in the bag 18 is sucked by the air pump 12 to be discharged automatically to make the bag empty for preparation to the next collection.

Thus, in the shown embodiment, the bag 18 is employed in place of the gas volumeter, and the bag 18 may be a container like a vinyl bag. Accordingly, the bag 18 can be transported in the folded condition and can be quite light in weight. Also, the bag 18 can be externally connected, and the suction amount can be arbitrarily varied by varying the size of the bag 18.

On the other hand, the pressure switch 30 can be constructed with a microswitch, a pressure receiving portion of rubber, a plastic tube and so forth. It is possible to construct that when the bag 18 is filled with air and the air pressure in the bag 18 is slightly elevated, the microswitch is operated by the pressure. Accordingly, since suction amount per one time is determined to be constant depending upon the volume of the bag 18, switching operation with reading the gas volumeter or with observing the scale as in the prior art becomes unnecessary. Therefore, while the gas volumeter is constructed as precision mechanical equipment in the prior art, it is expensive and requires sufficient attention in handling. However, the shown embodiment does not require such attention at all. Also, as for the bag 18, various sizes are available in the market as the gas containers to be used for gas analysis, they may be utilized with preliminarily measuring the volumes thereof.

On the other hand, in the gas collecting system 10, after completion of collection in one cycle, in order to prepare for next collection, it becomes necessary to discharge the air in the bag 18. By switching the switching cock 34 housed within the auxiliary receptacle box 42, the flow passage of the air pump 12 is reversed to automatically discharge the gas within the bag 18 with maintaining the bag 18 in the mounted position. Accordingly, operation ability and workability become superior. Particularly, by forming the switching cock 34 as modified four-way type with improving three-way cock of polyethylene, for example, switching of the flow passage can be performed by one-touch operation by one switching operation. On the other hand, the switching cock 34 is associated with a not shown speed adjusting switch varying the drive voltage of the air pump 12 to be constructed so that the air pump 12 is driven at low speed upon collection of gas and at high speed upon discharging, associating with switching of the switching cock 34.

Here, a condensation rate of the gas component of the inspection objective gas in the collecting liquid 28 collected by the impinger 14 is determined by a ratio of the collecting liquid amount and the sucked ambient air amount. Since the impinger 14 is made compact, condensation and collection can be done by small amount (1 to 3 ml) of collecting liquid 28. Therefore, high condensation can be obtained with small ambient air suction amount, and the volume of the bag 18 can be made small to be 1 to 5 liters. On the other hand, upon color comparison analysis, since the impinger 14 can be used as the reaction vessel and color comparison tube as it is, it becomes unnecessary to transfer the collecting liquid 28 or sample a part of the collecting liquid 28 for analysis, and operability in chemical analysis is improved. Here, color comparison analysis means an analyzing method performed by adding a reagent to a solution, in which the inspection objective gas is collected, for indicating a particular color by chemical reactions to measure light transparency by color density and to measure concentration of the gas component. On the other hand, in the impinger 14, small-size glass test tube available from the market can be used to make the impinger 14 for facilitating handling at quite a low cost, in comparison to the conventional impinger.

On the impinger 14, the elastic cap 22 is fitted, and large size injection needle form metallic capillaries are employed for the tube 24 and the tube 26 to be set to the elastic cap 22. These tube 24 and tube 26 may certainly provide flow passages for the air by simply piercing through the elastic cap 22. Since the impinger may be operated in the condition where the elastic cap 22 is maintained in the fitted condition, the collecting liquid 28 will not spill even if the impinger 14 is erroneously turned over. Also, the collecting liquid 28 and the reagents for reaction can be filled into the impinger 14 by an injector with maintaining the elastic cap 22 in the set condition, whereby operation ability and security can be improved. The tube 24 and the tube 26 have small diameter by constructing as the capillaries so that bubble discharged from the tip end of the tube 24 into the collecting liquid 28 becomes smaller to enhance dissolving ability of the gas component and thus to improve collection efficiency.

Furthermore, upon releasing the tube 24 and the tube 26 after completion of collecting operation of the inspection objective gas, the interior of the impinger 14 is slightly lowered in pressure to suck the collecting liquid 28 residing within the tube 24 into the impinger 14. Therefore, washing of the tube 24 and tube 26 becomes unnecessary. Also, contamination by the residual liquid can be prevented. In addition, the tip ends of the tube 24 and the tube 26 are formed as closed needle to facilitate insertion into the elastic cap 22. Communication openings for the gas is formed as transverse holes in the vicinity of the tip end portion 24a and 26a to prevent plugging by chips of the rubber.

The tube 24 formed as metallic capillary may also serve as a resistance tube for the gas flow to stabilize gas flow rate. Therefore, gas flow rate (flow velocity) can be appropriately controlled to make collection ratio of the inspection objective gas uniform to improve precision of inspection of the inspection objective gas. Also, by selecting length and thickness of the tube 24 and the tube 26, the flow velocity can be controlled with little influence of performance of the air pump 12, and thus can be stabilized. Thus, monitoring by the instantaneous flowmeter or needle valve as was required in the prior art can be eliminated so as to permit collecting operation without paying attention for adjustment of the flow rate. While the foregoing discloses the case where the tube 24 and the tube 26 are formed as metallic capillaries, they are not specified to the shown construction but can be glass or plastic capillaries.

As set forth above, the shown embodiment of the gas collecting system 10 has a simple construction, in which the impinger 14 and the drying agent tube 16 are provided in the suction port 12a of the portable air pump 12 and the bag 18 is provided in the exhaust port 12b. Therefore, as shown in FIG. 3, respective of these components can be assembled into compact construction as a whole. Accordingly, the gas collecting system 10 assembled as set forth above is portable to demonstrate superior transporting ability and to make adjustment of assembling of the material and component unnecessary, thus permits simple collection of air at an arbitrary site. Therefore, handling can be simplified to require no skill, and permits anybody's use. In this case, by using with setting on a tripod mount for camera or so forth, adjustment of height can be done easily, and the shown system requires less space. Accordingly, the gas collecting system is quite simple in construction and is inexpensive and compact.

Here, the structure of the elastic cap 22 employed in the foregoing first embodiment will be discussed.

Figure 4:
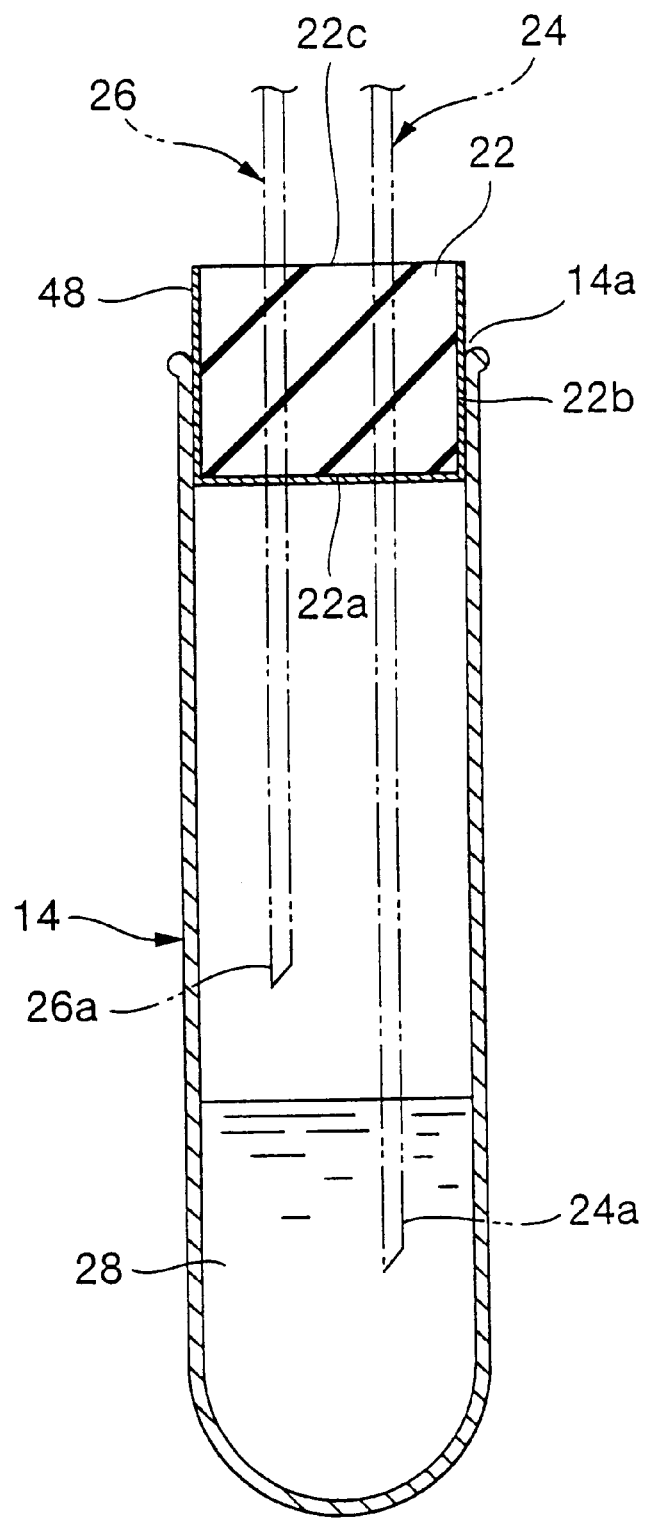
FIG. 4 is an enlarged section of a cap to be employed in an impinger of the gas collecting system according to the present invention.

As shown in FIG. 4, the elastic cap 22 closing the upper end opening portion 14a of the impinger 14 is formed of a synthetic rubber. At least a portion of the elastic cap 22 formed of the synthetic rubber, which is inserted into the impinger 14 with closing the upper end opening portion 14a, is coated by an insulation layer 48 formed of a material not influencing the collecting liquid 28.

Namely, the elastic cap 22 is designed so that the bottom surface 22a and the substantially lower half of side surface 22b thereof is inserted into the impinger 14. In order to cover the bottom surface 22a and the side surface 22b entirely, the insulation layer 48 is integrally coated or adhered as a thin film layer. The insulation layer 48 is not limited to the bottom surface 22a and the side surface 22b of the elastic cap 22 but may coat the overall surfaces including the upper surface 22c, as a matter of course. The insulation layer 48 itself is selected so as not to influence the collecting liquid 28 and a soft material having an appropriate elasticity so as not to spoil sealing ability of the elastic cap 22. For example, resin materials, such as polyethylene, vinylidene chloride resin, fluoroplastic, vinyl chloride and the like or metal foil, such as tin and the like may be used.

The elastic cap 22 of the impinger 14 which is also used as the color comparison tube, is coated the bottom surface 22a and the side surface 22b, which is inserted into the upper surface opening portion 14a of the impinger 14, with the insulation layer 48. Therefore, the gas component generated from the elastic cap 22 is blocked from penetrating into the impinger 14 by the insulation layer 48. Thus, even when the collecting liquid is preliminarily filled in the impinger 14 before implementation of analysis of the inspection objective gas, the gas component generated in the elastic cap 22 does not influence the collecting liquid 28. Therefore, it has become possible to store for a long period in a condition where the collection liquid 28 is filled in the impinger 14.

Figure 5:
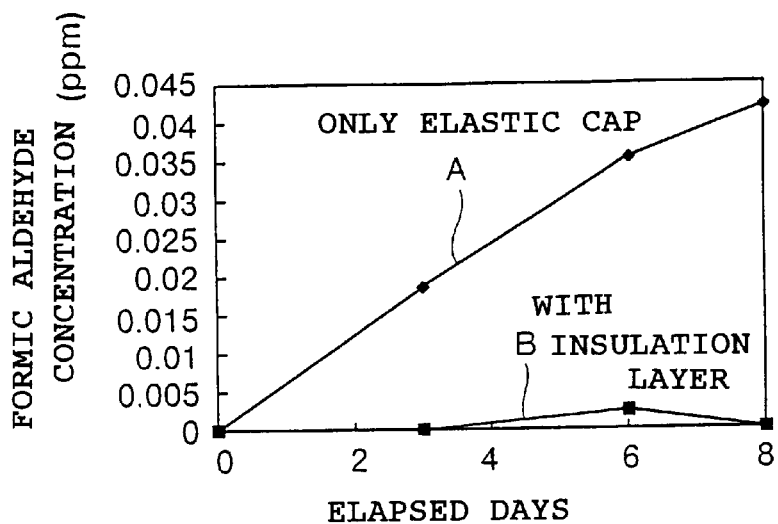
FIG. 5 is a graph comparing the storing condition of a collecting liquid filled in the impinger for a case of a normal cap and a case of the cap shown in FIG. 4.

FIG. 5 is a graph showing comparison of variation of concentration of formic aldehyde when the collecting liquid 28 is filled in the impinger to which the normal elastic cap is set, and the impinger 14 to which the shown embodiment of the elastic cap 22 having the insulative layer 48. Characteristics A shows the characteristics of the impinger closed only by the elastic cap, and characteristics B shows the characteristics of the shown embodiment, which the impinger 14 is closed by elastic cap 22 with the insulation layer 48. Of course, the graph shows influence of the elastic cap to the collecting liquid 28 in the condition where gas collection is not performed.

Namely, as shown by the characteristics A, in the impinger, for which the insulation layer is not provided on the elastic cap, certain gas component generated from the elastic cap influences the collecting liquid 28 associating with elapsing of days to increase concentration substantially proportional (about 0.04 ppm in eight days) as if formic aldehyde is sucked. On the other hand, in the shown embodiment of the impinger 14 employing the elastic cap 22 with the insulation layer 48, a peak (about 0.0025 ppm) is reached after elapsing of six days with slight increase between three to eight days, but it is extinguished after elapsing of eight days as shown by the characteristics B. It can be appreciated that the gas component generated from the elastic cap 22 gives little influence for the collecting liquid 28.

Therefore, when the elastic cap 22 coated by the insulation layer 48 is employed, it becomes possible to store for a long period in a condition where the collecting liquid is filled in the impinger 14. Therefore, upon performing gas analysis, the impinger 14 containing preliminarily prepared collecting liquid 28 is set on the gas collecting system 10. By this, analyzing operation can be significantly simplified and performed quickly. Also, since storage for long period becomes possible, it becomes possible to trade in the condition where the collecting liquid 28 is filled in the impinger 14 to significantly enhance a commercial value in comparison with the case where the impinger 14 and the collecting liquid 28 are sold separately.

Figure 6:
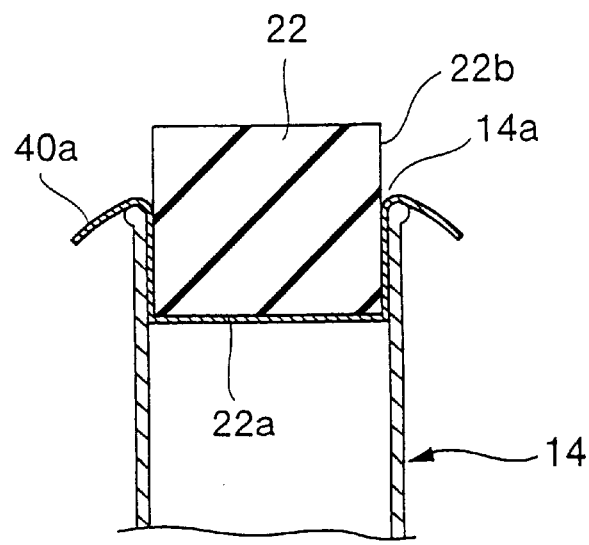
FIG. 6 is an enlarged section of the major part showing a modification of the cap of FIG. 4.

The insulation layer 48 is not limited to be coated or adhered, but can be formed as an independent sheet as shown in FIG. 6. In this case, the insulation layer 48a is formed into a size substantially covering the bottom surface 22a and the side surface 22b of the elastic cap 22 so that, after covering the upper end opening portion 14a of the impinger 14 by placing the center portion of the insulation layer 48a thereover, the elastic cap 22 is inserted into the upper end opening portion 14a with depressing the insulation layer 48a. Even with such construction, the portion of the elastic cap 22 to be inserted into the impinger 14 is covered with the insulation layer 48a to isolate the elastic cap 22 from the interior of the impinger 14.

Next, the structure of the pressure switch 30 employed in the first embodiment will be discussed in detail.

Figure 7:
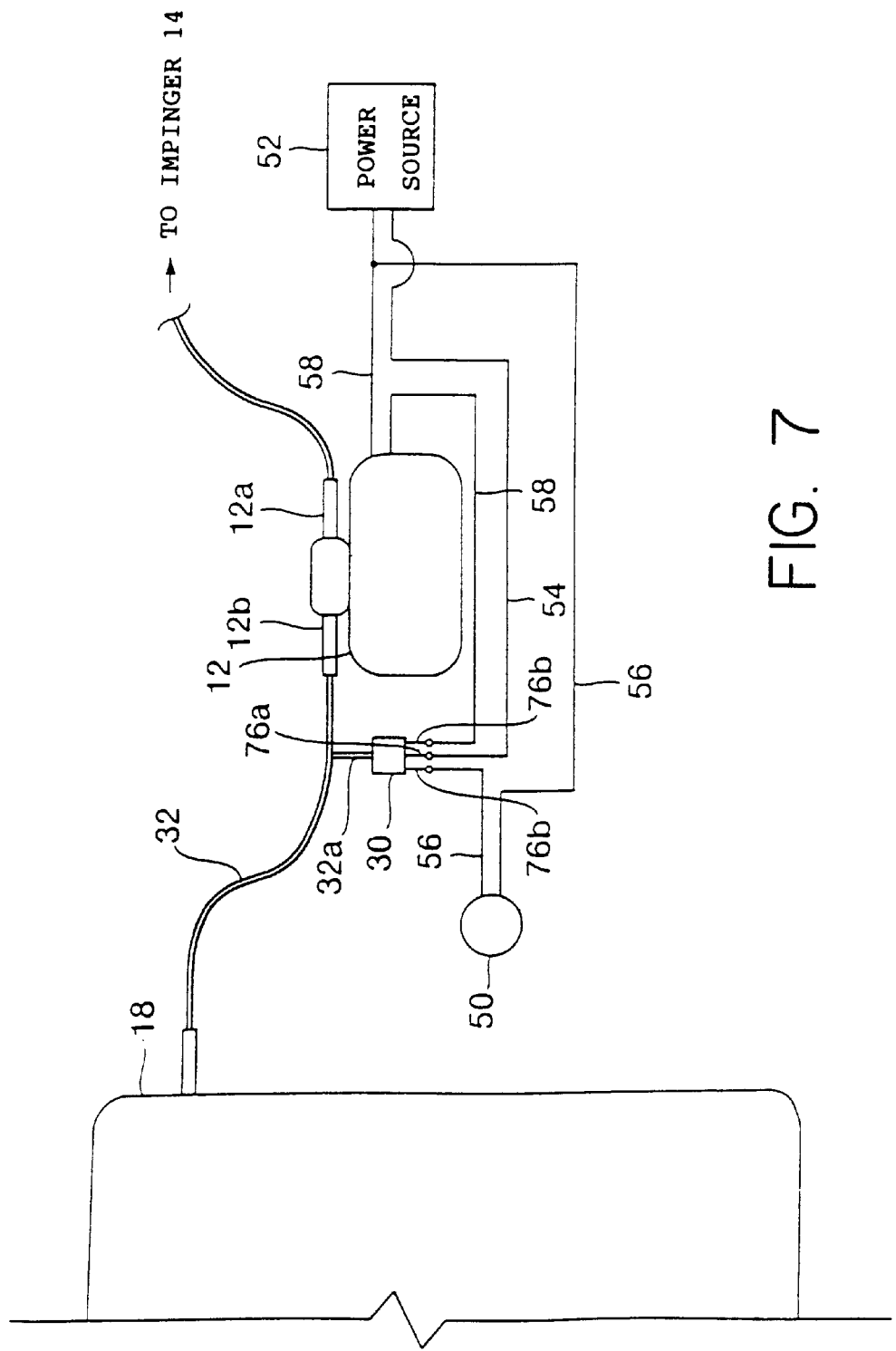
FIG. 7 is a circuit diagram of a pressure switch to be employed in the gas collecting system according to the present invention.

FIG. 7 shows the air pump 12 and the bag 18, and the periphery of the connecting portion. The pressure switch 30 is connected to a branch portion 32a disposed between the air pump 12 and the bag 18 and extended from an intermediate portion of the discharge tube 32 flowing the gas accumulated within the bag 18 from the air pump 12, and is actuated upon detecting a pressure within the bag 18. On the other hand, a buzzer 50 is provided on the gas collecting system 10. The pressure switch 30 is disposed between the buzzer 50 and the air pump 12, and a power source 52 supplying an operation power thereto for controlling ON/OFF actuation of the buzzer 50 and the air pump 12. Namely, a power source line 54 extended from the power source 52, a buzzer side line 56 extended from the switch 30 and connected again to the power source via the buzzer 50 and the air pump 12, and an air pump side line 58 are connected to the pressure switch 30 for electrically connecting and opening the buzzer side line 56 and the air pump side line 58 in respect of the power source line 54.

Figure 8:
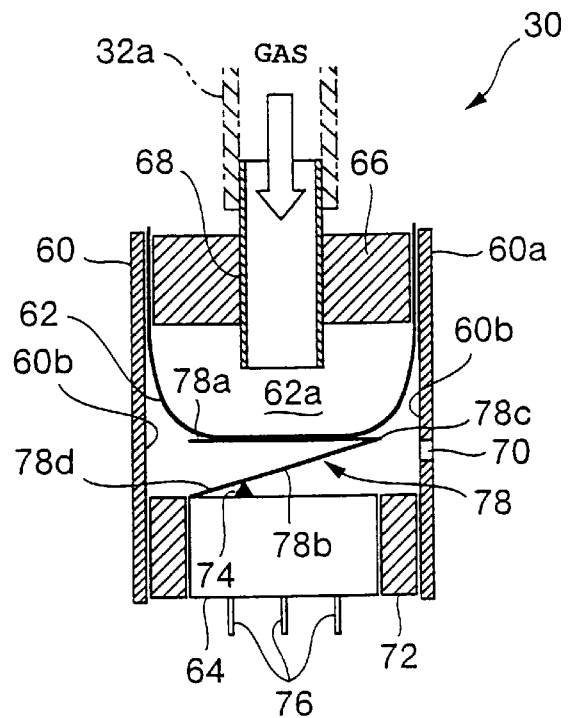
FIG. 8 is a section showing a construction of the pressure switch shown in FIG. 7.
Figure 9:
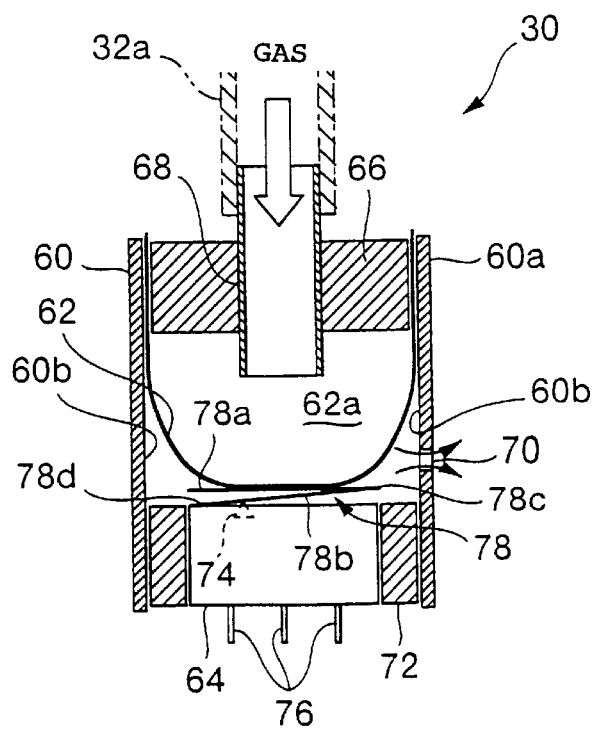
FIG. 9 is a section showing an operating condition of the pressure switch shown in FIG. 7.
Figure 10:
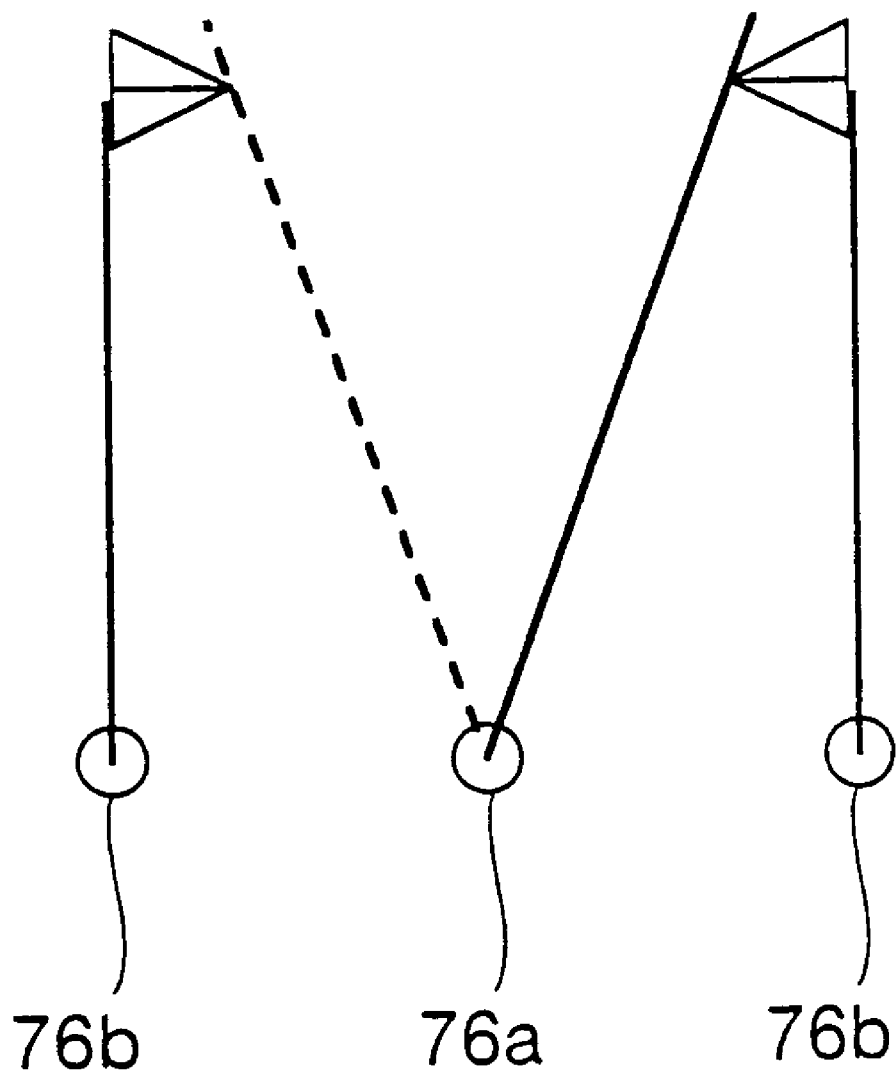
FIG. 10 is a diagrammatic illustration of a push-type switch body to be provided in the pressure switch shown in FIG. 7.

As shown in FIGS. 8 and 9, the pressure switch 30 is mainly constructed with an outer casing 60 formed into a hollow cylindrical shaped configuration and serving as a guide, an extending member 62 arranged in an upper portion within the outer casing 60, and a depression type switch body 64 arranged in a lower portion within the outer casing 60.

Here, the extending member 62 is a bag shaped receptacle body of reversed bell shaped configuration expandably formed of a material having flexibility, such as a rubber membrane, and can be formed, for example, by a medical finger sac available in the market, and has a receptacle portion 62a which can sealingly receive the gas therein. The peripheral edge portion of the upper end opening of the extending member 62 is sealingly clamped and engaged between the upper opening end portion 60a and a rubber plug body 66 received with closing the same therein. The gas induction pipe 68 is provided through the center portion of the plug body 66. On the tip end portion of the gas induction pipe 68, the branch pipe 32a of the discharge pipe 32 is connected to establish communication between the receptacle portion 62a of the extending member 62 and the interior portion of the bag 18 for introducing gas into the receptacle portion 62a of the extending member 62. When the gas is not introduced into the receptacle portion 62a, the extending member 62 is placed in entirely flexed condition as shown in FIG. 8. When the gas is introduced into the receptacle portion 62a via the gas induction pipe 68, the volume is increased to make the external shape greater as shown in FIG. 9. Then, once the gas in the receptacle portion 62a is extinguished, it returns to the original flexed condition.

On the other hand, the outer casing 60 is provided surrounding the peripheral side of the extending member 62. Namely, when the extending member 62 is expanded, the outer casing 60 restricts expansion of the extending member 62 with inner walls 60b from the side portion, and, in turn, permits expansion in the axial direction, here, downward. By this, the extending portion 62 is expanded with being guided toward the push type switch body 64 by the inner walls 60b of the outer casing 60. On the other hand, in the inner walls 60b of the outer casing 60, a communication hole 70 for certainly providing communication with the outside is formed so that the air between the outer casing 60 and the extending member 62 is introduced and discharged through the communication hole 70 depending upon expansion and contraction of the extending member 62.

On the other hand, the push type switch body 64 is fixed in the lower portion on the inner side of the outer casing 60 via a rubber mounting member 72 disposed on the inner periphery in tightly sealing position. The switch body 64 has an operating portion 74 provided on the inner surface of the outer casing 60 with directing toward the extending member 62 and two, three or more of terminals 76 provided in a position exposed to the outside of the outer casing 60. The operating portion 74 is urged outward from the switch body 64 by an urging member, such as a not shown spring housed within the switch body 64 to be depressed into the switch body 64 when it is depressed, as shown in FIG. 9, and to return to the original position when depression is removed. Then, between the operating portion 74 and the extending member 62, an actuating member 78 is provided for transmitting an expansion force of the extending member 62 to the operating portion 74 of the switch body 64. The actuating member 78 includes two upper and lower plate members 78a and 78b connected via a hinge portion 78c and is constructed expandably. The lower end portion of the actuating member 78 is connected to the operating portion 74 of the switch body 64 in the vicinity thereof via a hinge portion 78d. On the other hand, the upper plate member 78a is provided in contact with the outer bottom surface of the extending member 62. Then, the actuating member 78 is pressed downward in the outer casing 60 via the hinge portion 78c by expansion of the extending member 62, and the lower plate member 78b contacts with the operating portion 74 to depress the latter. On the other hand, upon contraction of the extending member 62, the operating portion 74 is released from depression and is pushed outwardly by the urging force of the urging member housed within the switch body 64 to contact with the lower plate member 78b of the actuating member 78 to push the latter for extending the actuating member 78. By this, the extending member 62 is returned in the contracting direction as becoming smaller in its outer shape and returned to the original condition. Thus, the operating portion 74 is either depressed or opened depending upon expansion and contraction of the extending member 62.

Depending upon depression and release of the operating portion 74 as set forth above, the switch body 64 establishes and releases mutual electrical connection of the respective terminals 76 of the switch body 64. Namely, the switch construction of the switch body 64 has one common terminal 76a in a plurality of terminals. For the common terminal 76a, either of the remaining terminals 76 is selectively connected as a switching terminal 76b to form a changeover switch construction. When the operating portion 74 is depressed, the one switching terminal 76b is connected to the common terminal 76a, and the other is opened. On the other hand, when the operating portion 74 is opened, the other switching terminal 76b is connected to the common terminal 76a and the one switching terminal is opened. As such switch body 64, a microswitch commercially available is preferably employed, in general.

In the pressure switch 30, the common terminal 76a is connected to the power source line 54, and the switching terminals 76b are respectively connected to the buzzer side line 56 and the air pump side line 58 so that when the extending member 62 is expanded by gas pressure, electrical communication between the air pump 12 and the power source 52 is switched from the established condition to the opened condition, and the electrical communication between the buzzer 50 and the power source 52 is switched from the opened condition to the established condition. Accordingly, in the gas collecting system 10, when the interior of the bag 18 is filled with a given amount of air, driving of the air pump 12 is automatically stopped to interrupt introduction of the ambient air from the inspection objective space. In conjunction therewith, the buzzer 50 can be actuated to report this.

In such pressure switch 30, the operating portion 74 of the switch body 64 is depressed by expansion of the extending member 62 to establish and open the connections between two, three or more terminals 76. Therefore, construction is simple to easily achieve reduction in cost and downsizing. On the other hand, since expansion of the extending member 62 can be guided by the outer casing 60, when it is applied to the gas collecting system 10 set forth above, it can satisfactorily detect the pressure even when the pressure to be detected is low. Further, since the commercially available micro-switch is used as the switch body 64, high reliability can be obtained with certainly achieving high durability. Also, by replacing the switch body 64 with other switch construction, switching function of the switch can be easily modified to widen application field and to achieve high general applicability. The setting of the pressure actuating the pressure switch 30 can be simply modified by appropriately selecting the switch body 64 in view of the urging force of the urging member and so forth, for example.

By the way, while the shown embodiment employs the extending member 62 formed into reversed bell shaped configuration, it can be of other shapes.

Next, the second embodiment of the gas collecting system according to the present invention basically includes a casing 82 covering the inspection objective space in a sealing condition from the outside to enclose the inspection objective gas discharged from the inspection object 80 filled therein, a sampling port 84 provided in the casing 82 for sampling the gas in the casing 82 containing the inspection objective gas, the air pump 12 sucking the gas within the casing 82 containing the inspection objective gas, a supply port 86 provided in the casing 82 for supplying a reference gas into the casing 82 in response to suction of the gas in the casing 82, the impinger 14 as the collection vessel filled with the collecting liquid 28 for collecting the inspection objective gas from the foregoing sampled gas, the tube 24 as the induction passage connected to the impinger 14 at one end and connected to the sampling port 84 at the other end for introducing the gas into the impinger 14, the tube 26 as the suction passage connected to the impinger 14 at one end and the suction port 12a of the air pump 12 at the other end for guiding the gas within the impinger 14 into the air pump 12, the bag 18 as a accumulating body serving as volumeter, connected to the discharge port 12b of the air pump 12, accumulating the gas discharged from the air pump 12, a capillary tube 88 as a capillary flow passage provided between the sampling port 84 and the bag 18 for lowering flow velocity of the sucked gas, the drying agent tube 16 provided between the bag 18 and the impinger 14 and serving as drying means for drying the gas, the pressure switch 30 detecting the internal pressure of the bag 18, a tube 36 as a bypass passage connecting the bag 18 to the suction port 12a of the air pump 12 bypassing the impinger 14, and the switching cock 34 serving as the switching means for switching flow passage to connect the bag 18 to either the discharge port 12b of the air pump 12 or the tube 36 and connecting the discharge port 12b of the air pump 12 to the ambient air opening passage 38 when the bag 18 is connected to the tube 36. The casing 82 has an opening 82a in its bottom portion. In the opening 82a, the packing 90 is provided for fitting the casing 82 to the inspection object 80 in airtight fashion. A filter 92 is connected to the supply port 86. The reference gas is the ambient air purified by the filter 92.

The second embodiment is directed to a type for sucking the gas into the casing 82 and simultaneously supplying the reference gas to the inspection object space sealed by the casing 82. While the construction of the downstream side from the impinger 14 is similar to that of the first embodiment, the construction on the upstream side of the impinger 14 is characteristic. Thus, only the characteristic portion is discussed.

Figure 11:
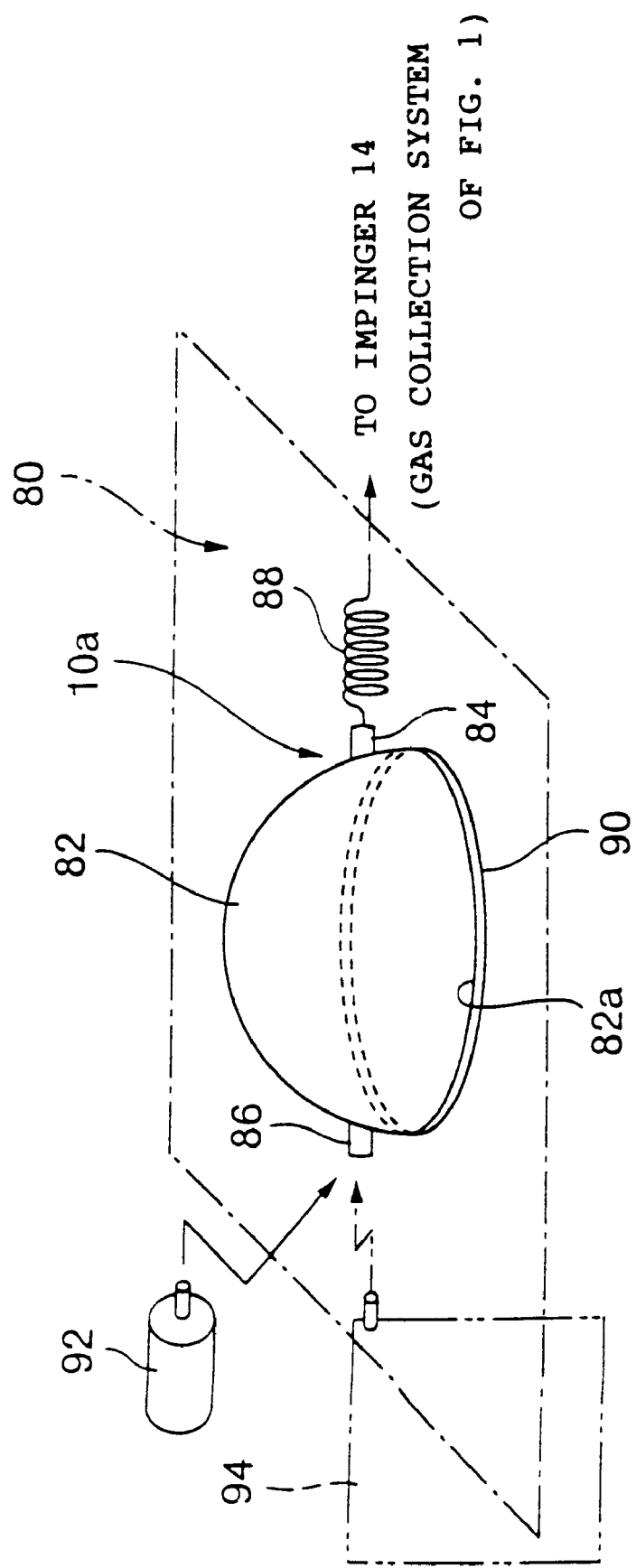
FIG. 11 is a perspective view showing a characteristic part of the second embodiment of the gas collecting system according to the present invention.

As shown in FIG. 11, the shown embodiment of the gas collecting system 10 includes the casing 82 formed in hemispherical form in a predetermined thickness with a transparent material. In the casing 82, the supply port 86 for taking the purified air as the reference gas into the casing 82, and the sampling port 84 supplying the gas in the casing 82, in which the inspection objective gas is admixed, into the gas collecting system 10 constructed as illustrated in FIG. 1, are provided in opposed positions. The air pump 12 is designed to forcedly suck the gas within the casing 82.

On the peripheral edge portion of the opening 82a of the casing 82, the packing 90 formed of soft rubber or the like is mounted so that the opening 82a is depressed onto the surface of the inspection object 80 via the packing 90. On the other hand, the capillary tube 88 wounded into spiral form as a resistance tube is connected to the sampling port 84. The flow velocity of the gas by suction of the air pump 12 is restricted at low speed by the capillary tube 88.

Ambient air purified through a catalyst filled in the filter 92 is employed as the purified air introduced into the casing 82 from the supply port 86. In this case, the catalyst filled in the filter 92 may be selected from activated charcoal, porous polymer beads, molecular sieve, chemical filter and so forth appropriately depending upon kind of the inspection objective gas. In FIG. 11, in place of the filter 92, a bag 94 as a reference gas receptacle body filled with the purification air employed in the reference gas or nitrogen gas or the like to be used as the reference gas, may be employed, and the bag 94 may be connected to the supply port 86 for introducing the reference gas in the bag 94 into the casing 82.

With the construction set forth above, in the shown embodiment of the gas collecting system 10a, the opening 82a of the casing 82 is urged onto the inspecting portion of the inspection object 80 under the condition where the capillary tube 88 connected to the sampling port 84 of the casing 82 is connected to the tube 24 of FIG. 1, and in conjunction therewith, the filter 92 is connected to the supply port 86 of the casing 82. At this time, on the opening 82a of the casing 82, the soft packing 90 is provided. Therefore, upon urging the opening 82a onto the surface of the inspection object 80, the opening 82a can be sealed by the packing 90. On the other hand, by forming the casing 82 transparent, checking of the installation condition or observation of the condition of the surface of the inspection object 80 can be easily achieved upon urging the casing 82 onto the inspection object 80.

Then, when the gas in the casing 82 is sucked from the sampling port 84 by the air pump 12, the air purified by the filter 92 is introduced into the casing 82 from the supply port 86, in the amount corresponding to the sucked amount. At this time, the inspection objective gas discharged from the inspection object 80 is collected in the enclosed casing 82. The collected inspection objective gas is admixed with the purified air introduced from the supply port 86 and then sucked from the sampling port 84 by the air pump 12. Then, the gas sucked for a predetermined period by the air pump 12 is accumulated in the bag 18. In conjunction therewith, inspection of the inspection objective gas contained in the collected gas is quantitatively analyzed by a chemical method using the impinger 14.

At this time, the discharge amount of the inspection objective gas from the portion covered by the casing 82 can be derived by the following equation (1).

(discharge amount of inspection objective gas)=(collected gas amount)/(opening area of casing×period of collecting operation)   (1)

On the other hand, in the shown embodiment, since the capillary tube 88 is connected to the sampling port 84 of the casing 82 to apply a resistance for the gas flow sucked from the interior of the casing 82 into the air pump 12 and to restrict the flow velocity low, when the gas within the casing 82 is sucked from the sampling port 84, the excessive negative pressure within the casing 82 can be prevented. Accordingly, it can avoid occurrence of penetration of the ambient air into the casing 82 through the sealed position, despite of the fact that the packing 90 is provided on the peripheral edge of the opening 82a of the casing 82 for sealing. Further, it also becomes possible to prevent the inspection objective gas from being forcedly discharged by the penetrating ambient air to enhance precision of analysis.

Figure 12:
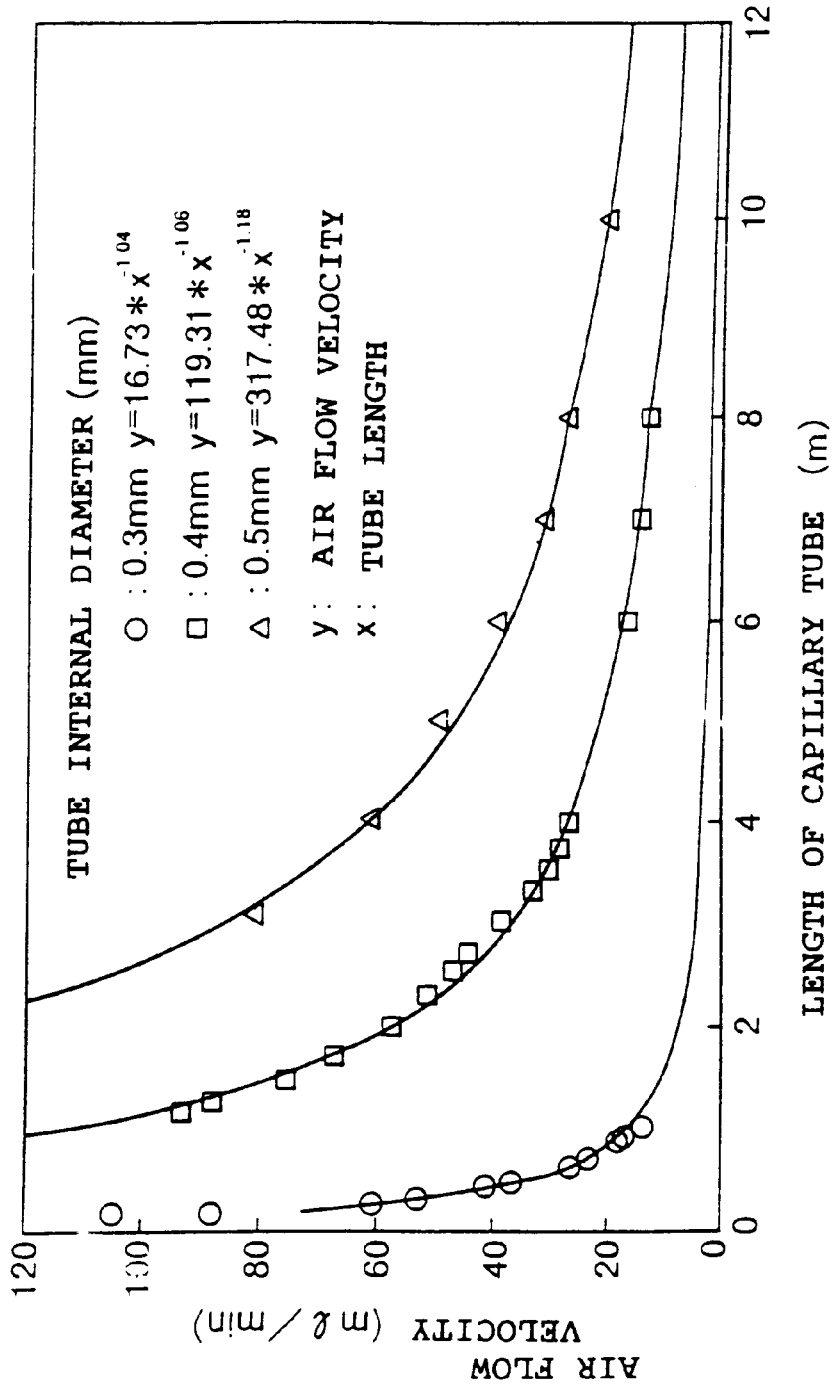
FIG. 12 is a graph showing a relationship between a length of a capillary tube to be employed in the gas collecting system shown in FIG. 11 and a flow rate.

The capillary 88 may stably and arbitrarily set the flow velocity of the air at low speed by appropriately selecting the internal diameter and the length of the tube as shown in FIG. 12. FIG. 12 shows a result of measurement of relationship between the length and the flow rate in the case where a tube formed of polytetrafluorocarbone (tradename: Teflon) is used as the capillary tube 88.

While the foregoing embodiment shows the case where the capillary tube 88 is connected to the sampling port 84, its construction is not specified to this. If the inspection objective gas may be absorbed into the inner surface of the capillary tube 88 to cause a measurement error, the capillary tube 88 may be connected on the downstream side of the air pump 12.

Accordingly, the shown embodiment of the gas collecting system 10a can perform inspection by collecting the inspection objective gas by simply pressing the casing 82 onto the surface of the inspection object 80. Therefore, it becomes unnecessary to cut a test piece from the inspection object 80. Therefore, not only for material inspection before construction, the inspection objective gas discharge amount can be easily measured at an arbitrary position even for the existing building after construction.

Further, many construction materials often include different kinds of materials in combination. For example, in case of combination where a finishing material is fixed on the concrete by applying a bonding agent, measurement becomes possible even after construction is completed. Therefore, it is quite useful in studying a gas discharging phenomenon. Furthermore, though measurement of the toxic gas in the building is only done as an average concentration in a large space in the prior art, it becomes possible to inspect gas amount per unit area as discharged from each individual material, thus facilitating the study for a measure preventing toxic gas generation according to the present gas collecting system 10*a*.

Discussion has been made for the case where the filter 92 is connected to the supply port 86 of the casing 82 to introduce the purified ambient air into the casing 82. However, when a bag 94 is used in place of the filter 92, the gas in the bag 94 is introduced into the casing 82 associating with suction of the gas from the sampling port 84.

In the foregoing embodiment, though discussion has been given for the case where the casing 82 is pressed onto the inspection object 80, it is possible to form the casing 82 as a closed box-shaped chamber to receive an inspection test piece and to collect gas discharged therefrom.

Further, by providing a stirring means within the casing 82 if required, it becomes possible to stir the gas containing the inspection objective gas within the casing 82 by the stirring means.

Next, the third embodiment of the gas collecting system according to the present invention is basically constructed with a casing 96 covering the inspection objective space from the outside in a sealed condition to enclose the inspection objective gas discharged from the inspection object 80 enclosed therein, a sampling port 98 provided in the casing 96 and sampling the gas containing the inspection objective gas within the casing 96, the air pump 12 sucking the gas from the inspection objective space within the casing 96, the impinger 14 as the collecting vessel filled with the collecting liquid 28 for collecting the inspection objective gas from the foregoing gas, the tube 24 connected to the impinger 14 at one end and to the sampling port 98 at the other end and serving as an induction passage for introducing the gas into the impinger 14, the tube 26 connected to the impinger 14 at one end and the induction port 12*a* of the air pump 12 at the other end and serving as the suction passage introducing the gas in the impinger 14 into the air pump 12, the bag 18 as an accumulation body serving as a volumeter, connected to the discharge port 12*b* of the air pump 12 and accumulating the gas discharged from the air pump 12, the drying agent tube 16 provided between the bag 18 and the impinger 14 and serving as the drying means for drying the gas, the pressure switch 30 detecting the internal pressure of the bag 18, the tube 36 serving as the bypass passage connecting the bag 18 to the suction port 12*a* of the air pump 12 bypassing the impinger 14, the switching cock 34 serving as the switching means for switching the passage so as to connect the bag 18 to either the discharge port 12*b* of the air pump 12 or the tube 36 and to connect the discharge portion 12*b* of the air pump 12 to the ambient air opening passage 38 when the bag 18 is connected to the tube 36, a first envelope 100 serving as an internal pressure maintaining bag provided within the casing-96 and being sealingly expandable, a tube 102 connected to the first envelope 100 by extending through the casing 96 and serving as a pressure introducing passage for introducing a pressure adjusting gas for expanding the first envelope 100 according to lowering of the internal pressure of the casing 96, a second envelope 104 provided in the casing 96 and sealingly expandable for serving as a volume varying bag, and a tube 106 connected to the second envelope 104 by extending through the casing 96, and serving as a gas introducing and discharging passage for supplying and discharging the volume adjusting gas to the second envelope 104 for modifying the volume within the casing 96 by expanding and contracting the second envelope 104.

The third embodiment is the type that the gas within the casing 96 is sucked with maintaining the gas pressure within the inspection objective space closed by the casing 96. Similarly to the second embodiment, in the shown embodiment, while the construction on the downstream side of the impinger 14 is the same as that of the first embodiment, the construction on the upstream side of the impinger 14 is characteristic. Therefore, discussion will be given only for the characteristic portion.

Figure 13:
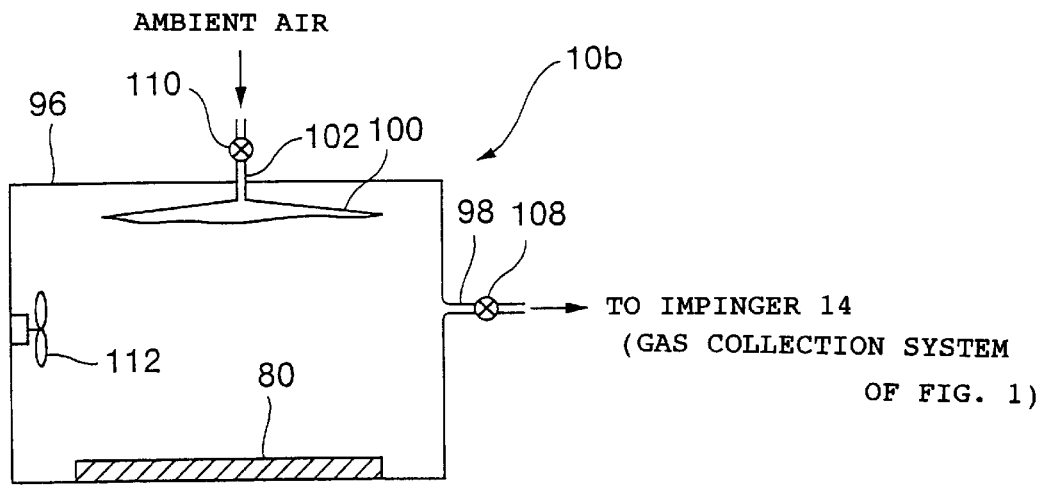
FIG. 13 is an illustration showing a characteristic part of the third embodiment of the gas collecting system according to the present invention.
Figure 14:
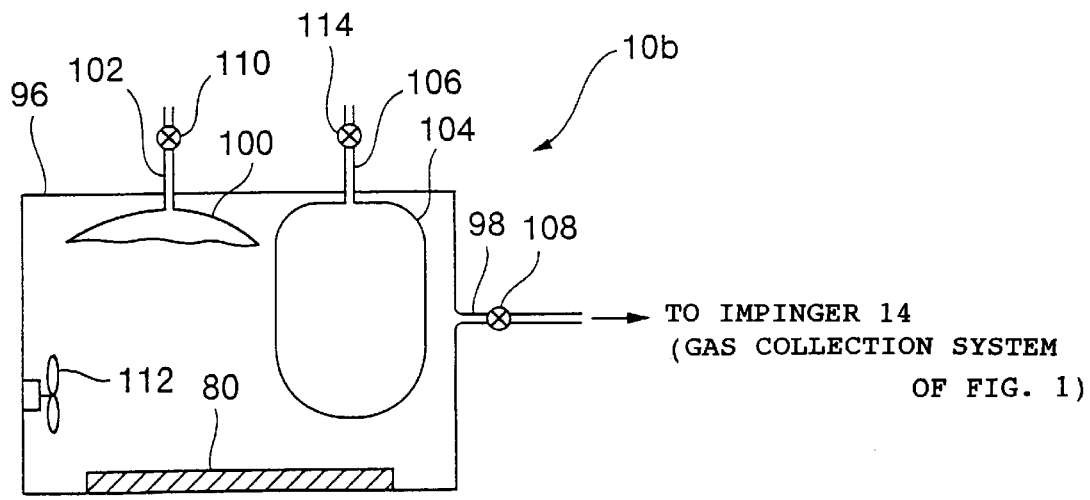
FIG. 14 is an illustration of a general construction showing a modification of the gas collecting system shown in FIG. 13.

For simplification of disclosure, first, FIG. 13 shows the case, in which only first envelope 100 is provided, and FIG. 14 shows the case where the second envelope 104 is additionally used.

As shown in FIG. 13, the shown embodiment of the gas collecting system 10*b* has the casing 96 for collecting the inspection objective gas discharged from the inspection object 80 by covering the inspection object 80 in the gas-tight condition. The gas containing the inspection objective gas, within the casing 96 is supplied to the gas collecting system constructed as shown in FIG. 1 to perform analysis of the inspection objective gas in the gas.

The casing 96 is constructed as a chamber of a closed structure as shown in FIG. 13, so that the inspection object 80, such as a plywood piece or the like, as the inspection material piece, is housed within the casing 96 as a form of chamber. The sampling port 98 for the interior gas is provided in the casing 96. An opening and closing cock 108 as a port opening and closing means is provided in the sampling port 98. The sampling port 98 is connected to the impinger 14 of the gas collecting system 10 via the tube 24. Within the casing 96, the expandable first envelope 100 is provided. Into the first envelope 100, ambient air outside of the casing is freely introduced via a tube 102.

The first envelope 100 is preferably formed with a flexible thin film having high flexibility so that a resistance is significantly small, when the first envelope 100 is expanded. Then, the tube 102 communicated with the first envelope 100 is sealingly mounted through an upper plate of the casing 96 so that the ambient air may be introduced freely into the first envelope 100 by maintaining a cock 110 open, which serves as a pressure introducing opening and closing means of the tube 102. On the side surface in the casing 96, a stirrer 112 as stirring means is mounted at a portion not causing interference with the first envelope 100 when it is expanded. By the stirrer 112, the gas in the casing 96 is stirred to be uniformly mixed with the discharged inspection objective gas.

The collecting operation of the inspection objective gas by the gas collecting system 10*b* is similar to that of the first embodiment. The gas in the casing 96 is sucked by the air pump 12 and the inspection objective gas in the gas is collected by the impinger 14. In conjunction therewith, the gas discharged from the air pump 12 is accumulated in the bag 18 serving as a volumeter.

Particularly, in the shown embodiment, a released amount of the inspection objective gas is derived as follow. After first gas sampling by the gas collecting system 10b, a predetermined elapsed time is measured. After the predetermined period, next gas sampling and gas concentration measurement is performed to derive the released amount of the inspection objective gas by the following equation (2).

$$Q = \{C2 \ (Vo-Vs) - C1 \cdot Vo\}(1/T) \tag{2}$$

where

Q: gas generation amount from material E to be inspected;

C1: first gas concentration measured value;

C2: second gas concentration after elapsing a period T;

Vo: gas volume of casing before first sampling;

Vs: sampling amount;

T: elapsed period to second sampling from first sampling.

Further, by repeating concentration measurement by gas sampling per arbitrary elapsed time, it also becomes possible to perform long term observation of variation in gas concentration and variation in gas generation amount in the casing according to the elapsed time.

On the other hand, in the shown embodiment of the gas collecting system 10b, the closed casing 96 is employed for collecting the inspection objective gas discharged from the inspection object 80, and the expandable first envelope 100 is provided within the casing 96 to permit introduction of the ambient air outside of the casing 96 into the first envelope 100. Accordingly, the inspection objective gas discharged from the inspection object 80 is enclosed within the casing 96. The inspection objective gas is increased according to elapsed time and concentration of the inspection objective gas within the casing 96 is increased.

Then, upon measurement of gas concentration, the air pump 12 is actuated by opening the opening and closing cock 108 of the sampling port 98. The gas containing the inspection objective gas within the casing 96 is then sucked into the impinger 14 through the sampling port 98. At this time, the pressure in the casing 96 in a closed condition is lowered depending upon suction amount of the gas. Then, by this pressure reduction, the first envelope 100 is expanded by introduction of the ambient air for a volume corresponding to the suction amount through the tube 102. Therefore, the pressure reduction amount in the interior of the casing 96 can be canceled by the expansion amount of the first envelope 100 to maintain the gas pressure within the casing 96 constant. At this time, the ambient air introduced from the outside is maintained within the first envelope 100 and is not mixed with the gas within the casing 96. Therefore, the inspection objective gas to be sampled will not be diluted. Accordingly, the concentration of the sampled inspection objective gas can be made high enough to permit significant improvement in precision in measurement upon gas analysis.

Further, since lowering of pressure within the casing 96 can be prevented, various defects to be caused by pressure reduction can be avoided. Namely, amount of the inspection objective gas to be discharged from the inspection object 80 can be increased by pressure reduction to make gas concentration higher than the normal state. However, in the shown embodiment, this promotion of discharging of the inspection objective gas is avoided to eliminate error in the gas concentration to be analyzed. Furthermore, considering pressure reducing function, significantly high pressure resistive sealing ability would be required for the casing 96. However, since the pressure reduction is not caused in the shown embodiment, it becomes unnecessary to increase strength of the casing 96 and to pay attention to sealing ability of the same. While the shown embodiment has been disclosed for the case where a single first envelope 100 is provided within the casing 96, it is possible to provide a plurality of first envelopes 100.

FIG. 14 shows a modification for the foregoing third embodiment, in which the same components to those in the third embodiment will be identified by the same reference numerals and redundant discussion will be omitted.

The shown modification of the gas collecting system 10b is provided two envelopes 100 and 104 within the casing 96, in which the first envelope 100 serves as an internal pressure maintaining bag, and the other second envelope 104 is used as a volume varying bag. The first envelope 100 is adapted to maintain the internal pressure within the casing 96 constant as shown in the third embodiment, in which when the gas within the casing 96 is sucked by the air pump 12 through the sampling port 98 upon starting of gas collecting operation, the ambient air is introduced from outside of the casing 96 into the first envelope 100 according to lowering of the gas pressure within the casing 96.

On the other hand, the second envelope 104 is used by closing the cock 114 as the opening and closing means for supplying and discharging gas, in a condition, where the air is preliminarily introduced through the tube 106 for expansion within the casing 96 before initiation of gas collecting operation. By maintaining the second envelope 104 in the expanded state, the actual volume within the casing 96 can be varied.

Accordingly, in the modification, when the released amount of the inspection objective gas from the inspection object 80 is small and the gas concentration in the casing 96 cannot reach the level enabling measurement unless leaving it for a long period, the second envelope 104 is expanded to make the net volume smaller. Even when the discharge amount of the inspection objective gas is small, high concentration gas can be generated in the casing 96 within a short period of time.

As set forth above, by providing the second envelope 104, the net volume in the casing 96 can be varied without varying size of the casing 96 itself. Therefore, troublesomeness for preparing a plurality kinds of casings 96 with different volumes and to exchange them as required, can be avoided.

Then, by making the net volume smaller using the second envelope 104, even when the inspection objective gas within the casing 96 is sampled, the ambient air outside of the casing 96 can be freely introduced into the first envelope 100 according to suction of the gas within the casing 96, and the gas pressure within the casing 96 can be maintained constant by expansion of the first envelope 100.

On the other hand, while the shown embodiment employed the one first envelope 100 and the one second envelope 104, respectively, the present invention is not limited to the embodiment and respective envelopes can be provided in plural.

Figure 15:
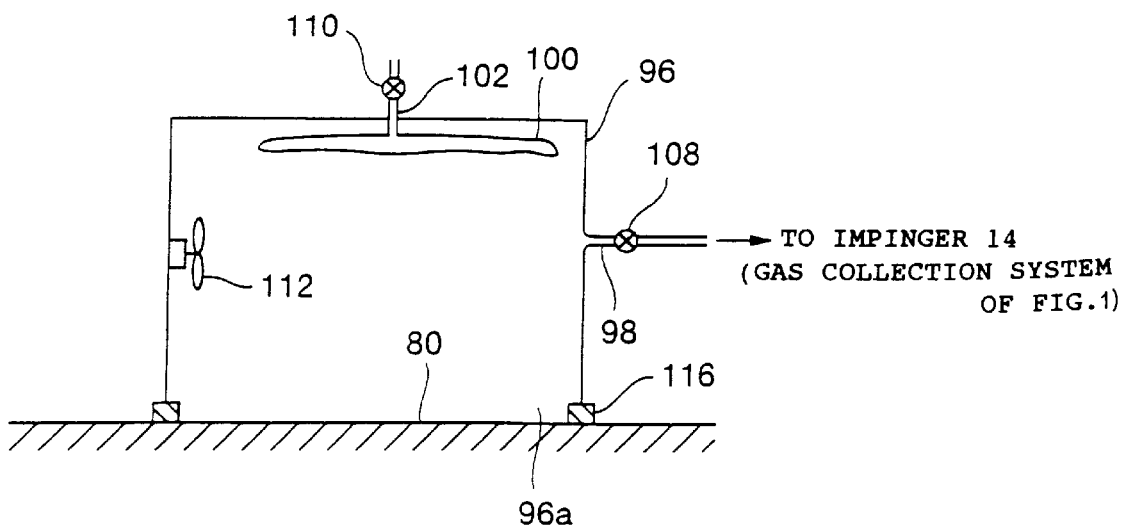
FIG. 15 is an illustration of a general construction showing another modification of the gas collecting system shown in FIG. 13.

FIG. 15 shows a further modification of the third embodiment, in which the same components to those of the third embodiment will be identified by the same reference numerals and redundant discussion will be omitted.

The modified gas collecting system 10b of the present embodiment is constructed such that the casing 96 is formed into a cover shaped configuration, in which the bottom portion is opened, and the packing 116 is mounted on the peripheral edge of the opening 96a.

Accordingly, in the shown modification, when the inspection object 80 cannot be cut as the test piece, such as the floor and wall of the existing building, the opening 96a of the casing 96 can maintain the interior of the casing 96 in an air-tight condition via the packing 116 of the peripheral edge of the opening 96a by fitting the opening 96a of the casing 96 onto the inspection object 80, such as existing floor and wall, in the air-tight fashion. Therefore, the inspection objective gas discharged from the floor or wall within the casing 96 may be collected, and the inspection objective gas collected within the casing 96 can be analyzed by the gas collecting system 10 shown in FIG. 1.

Further, in the shown modification, there is shown the case where the first envelope 100 for maintaining the gas pressure is provided similarly to the casing 96 of the chamber shape shown in the first embodiment (see FIG. 13). However, it should not be taken limitative, and it is possible to apply the first envelope 100 and the second envelope 104 similarly to the foregoing modification (see FIG. 14).

In the third embodiment and the modifications thereof, there is shown a case where the ambient air is introduced into the first envelope 100 and the second envelope 104 as the gas. However, the gas to be introduced is not specified to the ambient air. It is also possible to connect the respective tubes 102 and 106 to an adjusting gas receptacle body, such as a bomb filled with dedicated pressure adjusting gas or volume adjusting gas through tubes and to supply the dedicated gas enclosed within the receptacle body to the respective envelopes 100 and 104 through the respective tubes 102 and 106. On the other hand, as the gas to be filled in the casing 96, such gases must be selected that does not react with the inspection objective gas discharged from the inspection object 80.

Further, by forming the casing 96 with a transparent material, it becomes possible to check the setting condition of the inspection object 80 and to observe the condition of the surface of the inspection object 80.

The fourth embodiment of the gas collecting system according to the present invention basically includes a casing 118 covering the inspection objective space from outside and to enclose the inspection objective gas discharged from the inspection object 80 filled therein, a pair of gas circulating ports 120 and 122 provided in the casing 118 and for circulating the gas to the casing 118, an air pump 124 sucking the gas containing the inspection objective gas from the inspection objective space within the casing 118, an impinger 128 serving as a collecting vessel and filled with a collecting liquid 126 for collecting the inspection objective gas from the gas, a tube 130 connected to the impinger 128 at one end and to one of the gas circulating ports 120 of the casing 118 at the other end and serving as an induction flow passage for introducing the gas into the impinger 128, a tube 132 connected to the impinger 128 at one end and to a suction port 124a of the air pump 124 at the other end for serving as a suction flow passage introducing the gas within the impinger 128 into the air pump 124, a buffer 134 provided between the discharge port 124b of the air pump 124 and the other of the gas circulating port 122 of the casing 118 to buffer the gas pressure by temporarily accumulating the gas discharged from the air pump 124 and circulating and supplying the gas to the casing 118 again, and a humidity adjusting means provided between the buffer 134 and the impinger 128 for adjusting humidity of the circulated gas constant. The casing 118 has an opening 118a in the bottom portion. A packing 138 for fitting the casing 118 to the inspection object 80 in gas-tight fashion, is provided on the opening 118a. The buffer 134 is a bag capable of being expanded and contracted depending upon a difference between the pressure of the gas accumulated therein and the ambient pressure. The humidity adjusting means is a humidity conditioner bottle 136 filled with a humidity conditioner 140 prepared with a salt solution for adjusting humidity of the gas. The impinger 128 is formed with a transparent material for serving as a color comparison tube and also as a reaction tube, to which reagent reacting with the inspection objective gas is filled, and is provided in plural and in parallel relationship. Between the impinger 128 and one of the gas circulating port 120 of the casing 118, an electromagnetic valve 142 serving as switching means for selectively switching the connection between a plurality of impingers 128 and the casing 118 according to the elapsed time.

The fourth embodiment is the type that the gas in the inspection objective space enclosed by the casing 96 is circulated within a closed loop circuit for collecting the inspection objective gas.

Figure 16:
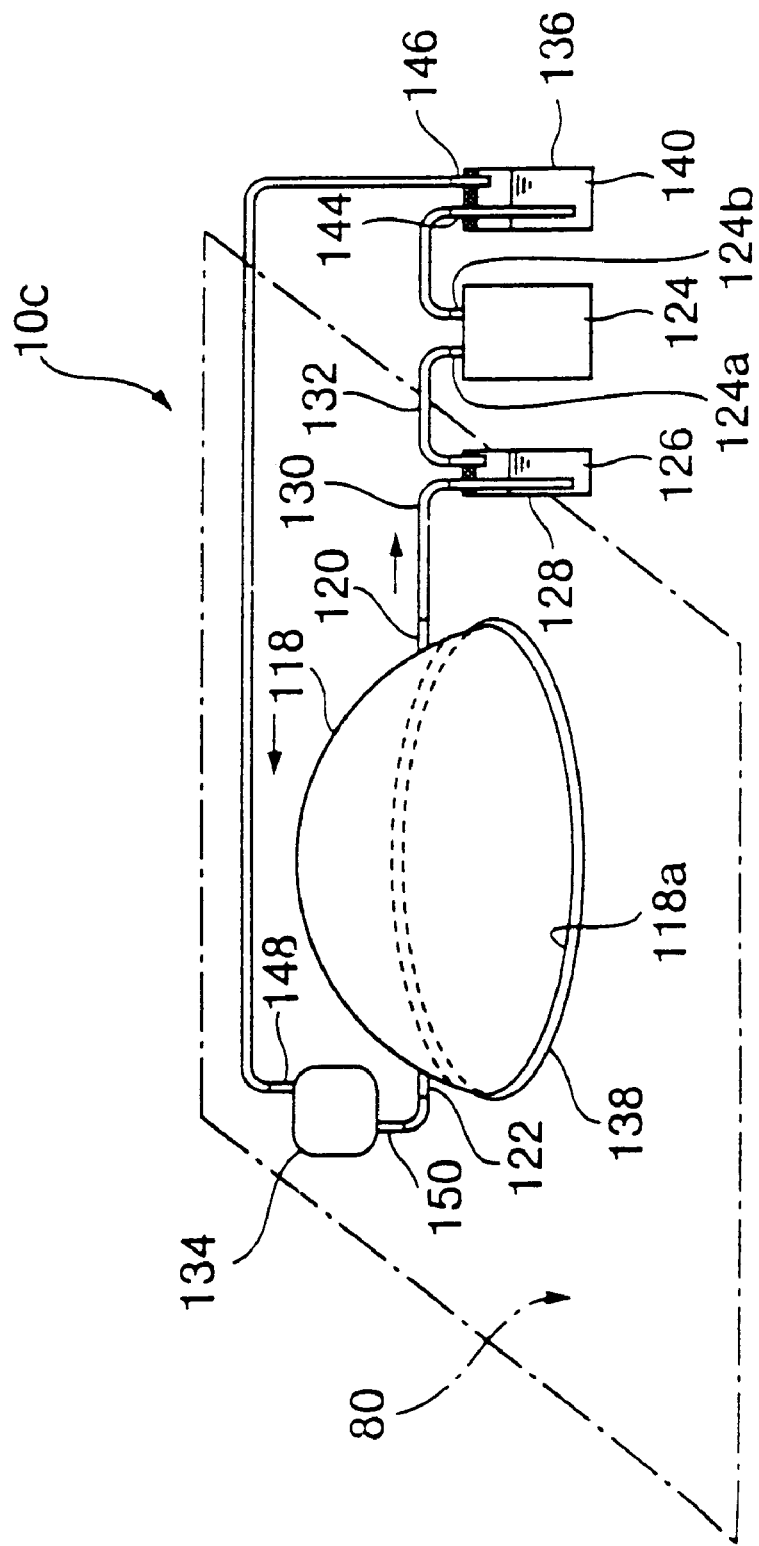
FIG. 16 is a circuit diagram of an entire circuit showing the fourth embodiment of the gas collecting system according to the present invention.
Figure 17:
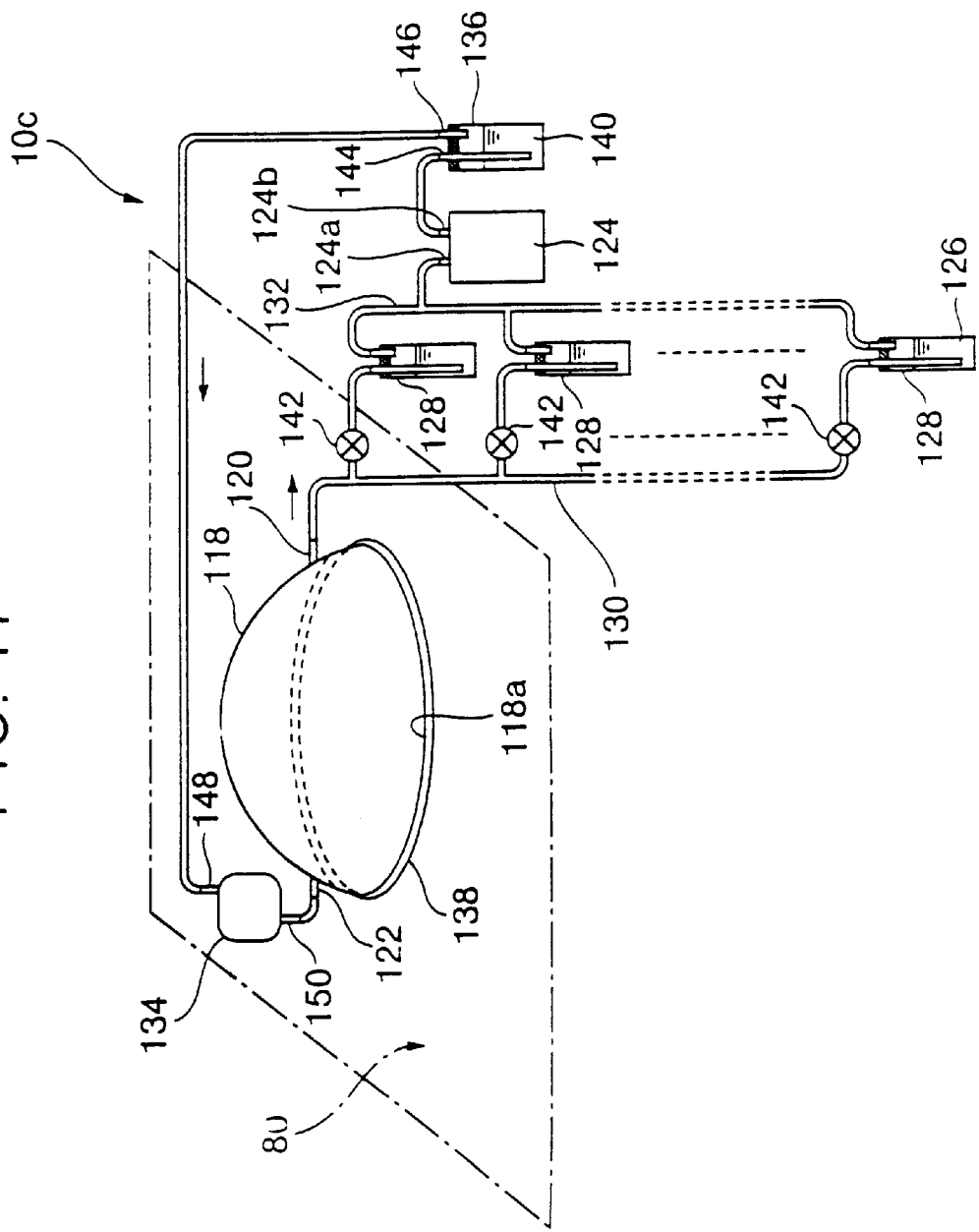
FIG. 17 is a circuit diagram of an entire circuit showing a modification of the gas collecting system shown in FIG. 16.

For simplification of discussion, a case where one impinger 128 is employed, illustrated in FIG. 16, and FIG. 17, shows the case where a plurality of impingers 128 are selectively switched by the electromagnetic valves 142.

As shown in FIG. 16, the shown embodiment of the gas collecting system 10c has the casing 118 formed into a hemisphere shape with a predetermined thickness from a transparent material for collecting the inspection objective gas naturally discharged from the inspecting portion. Around the casing 118, the impinger 128, the air pump 124, the humidity conditioner bottle 136 and the buffer 134 are connected in sequential order to form a closed flow passage for circulating the gas so that the gas in the casing 118 is forcedly sucked and circulated by the air pump 124, and the inspection objective gas is collected in the impinger 128.

In the casing 118, the gas circulating port 122 for taking the circulating gas and the gas circulating port 120 feeding the gas, in which the inspection objective gas is admixed, from the casing 118, are provided in opposed positions. On the peripheral edge of the opening 118a of the casing 118, the packing 138 formed of soft rubber or the like, is mounted. The packing 138 is pressed onto the surface of the inspection object 80 to sealingly enclose the interior of the casing 118.

The impinger 128, the tube 130 introducing gas thereinto, and the tube 132 thus feeding out the gas are similar to the impinger 14, the tubes 24 and 26 in the first embodiment. The portion of the cap of the impinger 128 covering the opening portion of the impinger 128 is also coated by the insulation layer of the material which does not influence the collecting liquid 126.

The air pump 124 is portable and driven by the battery, such as dry cells or the like, which is also similar to the first embodiment. The suction port 124a is connected to the impinger 128 via the tube 132, and the discharge port 124b is connected to the humidity conditioner bottle 136.

The humidity conditioner bottle 136 is formed by a cylindrical glass bottle. The upper end opening portion is closed by a rubber cap. A predetermined amount of the humidity conditioner 140, which is a salt solution, is filled into the humidity conditioner bottle 136. The tip end of a tube 144 introducing the gas is extended into the liquid of the humidity conditioner 140. The tip end of a tube 146 discharging the gas is extended above the liquid surface of the humidity conditioner 140, and bubbling of the introduced gas is carried out. The tube 144 is connected to the discharge port 124b of the air pump 124, and the tube 146 is connected to an induction opening 148 of the buffer 134 to maintain the humidity of the gas which is circulated to the casing 118. Namely, as the humidity conditioner 140, for example, a saturated solution of $BaCl_2.2H_2O$ which is a salt solution can be used. By passing air through the saturated solution at 24.5° C., air containing 88% of humidity is obtained, and the humidity of the passing air is maintained at a predetermined value. This is because the humidity of air in contact with the salt solution becomes constant in relation to the water vapor pressure of the salt solution, which depends on the kind and concentration of the salt solution and also the temperature. Since the values for various salts, regarding the above relations, are shown in chemical handbooks or the like, salts may be appropriately selected depending on the desired humidity.

The buffer 134 is formed with a plastic film or the like and is a bag variable of volume. In the buffer 134, an induction opening 148 introducing a flowing gas and a discharge opening 150 feeding out the interior gas are provided in opposed positions. The induction opening 148 is connected to the tube 146 from the humidity conditioner bottle 136, and in conjunction therewith, the discharge opening 150 is connected to the gas circulating portion 122 of the casing 118 so that the buffer 134 may be expanded depending upon the difference between the gas pressure introduced thereinto and the pressure of the ambient air to vary the volume thereof. Namely, when the internal pressure is elevated, the buffer 134 is expanded, and when the internal pressure is reduced, the buffer 134 is contracted, making the pressure difference between the inside and the outside to naturally be zero to enable circulation without causing variation of pressure of the gas.

Then, in the shown embodiment of the gas collecting system 10c, the opening 118a of the casing 118 is pressed onto the inspection object 80, and in conjunction therewith, the air pump 124 is driven. At this time, the packing 138 is provided on the opening 118a of the casing 118 to sealingly enclose the pressed portion by pressing on the surface of the inspection object 80. Further, since the casing 118 is formed transparently, the set condition can be checked and the condition of the surface of the inspection object 80 can be easily observed. Since the gas is sucked by the air pump 124, the gas within the casing 118 is introduced into the impinger 128 causing bubbling in the collecting liquid 126 in the impinger 128, and passes therethrough to be sucked into the air pump 124. The sucked gas is discharged from the discharge portion 124b of the air pump 124, and is returned to the interior of the casing 118 through the humidity conditioner bottle 136 and the buffer 134 for circulation. At this time, the inspection objective gas discharged from the inspection object 80 is captured in the collecting liquid 126 by bubbling through the collecting liquid 126 of the impinger 128 from the inside of the enclosed casing. Then, the gas returned into the casing 118 from the buffer 134 is purified, since the inspection objective gas is captured by the impinger 128. Also, the humidity thereof is also maintained constant by the humidity conditioner bottle 136.

Thus, collection of the inspection objective gas is performed for a predetermined period of time by circulating the gas, and quantitative analysis is performed by chemical method to obtain the amount of the inspection objective gas contained in the collecting liquid 126 of the impinger 128. At this time, the gas discharge amount can be derived by the foregoing equation (1).

On the other hand, since the buffer 134 is disposed in the circulating passage of the gas around the casing 118, the pressure difference between the inside and the outside of the circulating passage can be restricted. By this, it becomes possible to prevent pressure variation in the casing 118 by pulsation of the air pump 124 and variation of the peripheral atmospheric temperature. Namely, generation of the pressure difference due to pulsation of the air pump 124 and variation of the environmental temperature affects the increasing or decreasing of the pressure in respect of the inspection objective space, and causes leakage of the circulating gas to the outside or, conversely introduction of the external air to cause error in measurement. Increasing and decreasing of pressure acts on the gas discharging surface of the inspection object 80 to disable measurement of the discharged amount in natural condition. Such problem can be avoided by the shown embodiment to enhance the precision of inspection of the inspection objective gas. Also, since the gas is circulated without its variation in the pressure, increasing or decreasing of pressure will not be caused in the casing 118 so as to maintain satisfactory gas-tight seal between the casing 118 and the inspection object 80 to the extent of pressing through the packing 138.

Further, since the humidity conditioner bottle 136 is disposed in the circulation passage of the gas around the casing 118, the humidity of the circulated gas can be maintained at a predetermined value by the use of equilibrium of water vapor pressure of the salt solution. For some kinds of materials of the inspection object 80 and some kinds of the inspection objective gases, humidity of the circulating gas causes variation in the discharge amount of the inspection objective gas. However, this problem is prevented, and data quality is improved by the above humidity conditioning.

Furthermore, since a system to circulate the gas including the casing 118 is employed, the purified gas supply means, such as a purified gas supply device or a nitrogen gas supply device as an alternative becomes unnecessary. Due to this, the construction of the gas collecting system 10c is made simple, compact and inexpensive.

On the other hand, the shown embodiment of the gas collecting system 10c can perform not only inspection for the construction material, but also collection of the inspection objective gas from the material as it is used, namely at the arbitrary portion with respect to the building after completion of construction, similar to the second and third embodiment of the gas collecting systems 10a and 10b.

On the other hand, the casing may, of course, be a box shaped chamber receiving the inspection material piece as exemplified by the third embodiment.

In FIG. 17, a modification of the fourth embodiment is illustrated, in which a plurality of impingers 128 are provided for sequentially monitoring variation of the discharge amount of the inspection objective gas according to elapsed time.

In the gas collecting system 10c shown in FIG. 17, a plurality of the impingers 128 are provided in parallel, and the electromagnetic valves 142 for switching connection are provided between these impingers 128 and the casing 118, and the electromagnetic valve 142 is switched per every predetermined collection period. Switching of the electromagnetic valve 142 may be automated by a timer control. The shown modification is constructed so that connection of the impingers 128 is sequentially switched. The shown gas collecting system 10c is suitable for inspecting the discharge phenomenon of ammonia gas released from paint. Discharge amount (discharge speed) of the ammonia gas varies according to elapsed time from the time immediately after application of the paint to completion of curing. Therefore, by sequentially switching gas collection, it becomes possible to perform gas collection as time elapses to monitor the process thereof.

Finally, discussion will be given for a simple analyzing method of formic aldehyde to be implemented using the shown embodiment of the gas collecting system 10. The members such as the impingers 14, which are consumable articles to be exchanged, may be supplied as an analysis kit.

The analysis kit includes:

(i) 2N-KOH solution (aqueous sodium hydroxide having a normality of 2) is employed as the collecting liquid 28. Ten to twenty impingers 14 respectively filled with 2.0 ml of this collecting liquid;

(ii) one Bial bottle A (having volume of 50 to 100 ml) containing AHMT reagent;

(iii) one Bial bottle (having volume of 50 to 100 ml) containing $KIO_4$ reagent;

(iv) several plastic injectors (having volume of 1 ml);

(v) one impinger containing a standard color solution;

(vi) one sand glass (for 20 minutes); and (vii) one portable absorptiometer.

Next, discussion will be given for operating procedure for measurement of concentration of formic aldehyde by employing the foregoing analysis kit.

(I) At first, the impinger 14 is mounted on the gas collecting system 10 to suck the gas containing formic aldehyde. At this time, a standard gas suction amount of 3 liter and 10 minutes of standard required time are employed.

(II) 0.5 ml of AHMT reagent is taken from the Bial bottle A by an injector and added to the impinger 14. The impinger 14 is left in this condition for 15 to 20 minutes or longer. At this time, the sandglass is used.

(III) While the impinger 14 added with AHMT reagent is left, the standard color solution is set in the absorptiometer. Then, a dial is adjusted so that the indication value becomes a predetermined value.

(IV) 0.5 ml of $KIO_4$ reagent is taken from the Bial bottle B by an injector and added to the impinger 14.

(V) The impinger 14 is set in the absorptiometer to read the indication value, and the read value is obtained as the concentration of formic aldehyde.

Accordingly, in the analysis method of formic aldehyde in connection with this embodiment, the impinger 14 used in the analysis kit (i) can efficiently collect formic aldehyde in the gas to enhance collection efficiency by using 2N-KOH solution. Further, since the amount of the collecting liquid to be used is small, such as 2.0 ml, high condensation can be achieved even with small suction amount of the gas to facilitate detection even in low gas concentration. This is an appropriate concentration for certainly maintaining reaction ability of the AHMT reagent of (ii) which is added later, and it becomes unnecessary of after addition of alkali reagent.

On the other hand, AHMT reagent and $KIO_4$ reagent necessary for analysis are set with concentrations so that optimal reaction condition is obtained with respect to the collecting liquid 28 and so that the liquid amount to be added by the injector can be small. Namely, the composition of the AHMT reagent is prepared to have a composition of AHMT: 1%, and HCl: 1 mol/liter, and the composition of the $KIO_4$ reagent is prepared to have a composition of $KIO_4$: 1% and KOH: 0.25 N.

The additive amount of both reagents is set to be appropriate at 0.5 ml. This is because lower concentration than has been used conventionally requires about four times of additive amount, which lowers sensitivity of detection since color indication is lowered according to increase in overall liquid amount. On the other hand, when additive amount of the reagent is extremely reduced, a reading error of the liquid amount upon measuring by the injector becomes large. In the shown embodiment, since the use amount of both reagents at one time is small as 0.5 ml, many analyses are possible even when the amounts of the reagents to be carried are small.

Further, both reagents are made as kits being contained in the Bial bottles A and B of (ii) and (iii). These Bial bottles are bottles with rubber caps, and the reagents can be metered and taken by the injector without removing the caps. Therefore, the reagent may not be spilled or deposited on the hand.

Next, the standard color solution shown in (v) is preliminarily prepared in a laboratory, by taking a standard colored liquid, which corresponds to a color indication density upon reaction of a known amount of formic aldehyde with the reagent, as the standard color solution, and by enclosing the liquid in the same container as the impinger 14.

By enclosing the standard color solution in the impinger 14, and by adjusting the color comparison meter (absorptiometer) by taking the absorbance of the standard colored liquid as a standard for absorbance measurement, it becomes unnecessary to prepare an analytical curve by actually reacting the known amount of the formic aldehyde liquid upon each analysis. Further, since the color indication density of the liquid indicating color by reacting formic aldehyde becomes unstable making the color gradually more pale according to elapsed time, the standard colored liquid is prepared by using a red color dye having less fading effect.

On the other hand, since the color collecting system 10 has a construction which can constantly suck the predetermined amount of the gas, by adjusting the indication value of the absorptiometer to the predetermined value by the standard colored liquid on the premise of the suction gas amount, the indication value upon measurement of absorbance of an unknown sample can be directly read as the concentration of the formic aldehyde. Accordingly, calculation using molecular amount of formic aldehyde and a volume conversion coefficient or so forth becomes unnecessary. Also, a compact, lightweight and portable absorptiometer operated by dry cells is used, and it has a permselective filter of wavelength 530 nm.

Accordingly, in the shown embodiment, by employing the impinger 14, the AHMT reagent, $KIO_4$ reagent, the injector, the standard color solution, the sand glass and the portable absorptiometer formed as a kit, formic aldehyde concentration is measured by sucking the gas by the gas collecting system 10. Therefore, the system can be made compact to be easily handled and requires no special device. Thus, a result can be obtained within a short period and exactly at the place where the gas is collected. Further, expert knowledge and chemical calculation becomes unnecessary, and also, transferring or division of the sampled solution becomes unnecessary and requires no special measuring equipment such as whole pipette or the like for chemical analysis, which requires skill in handling.

The solution of the collecting liquid 28 and the reagents can be taken out by the injector without releasing the cap. Therefore, even if the bottleturns over, the content will never be spilled, which enables safe operation. Further, since analysis can be performed at the gas sampling site, it becomes unnecessary to pay any attention to transportation of the sample. Also, it becomes unnecessary to ask analysis for an external analyzing organization requiring high cost. Since result can be obtained at low cost, many measurements can be performed one by one as checking each test result.

As set forth above, in the shown embodiment of the formic aldehyde analyzing method, the measurement of concentration of formic aldehyde requires no expert knowledge, and can be carried out easily by simple operations at low cost and within a short period at the exact place. Therefore, even when inspection is performed within a new building, a large amount of inspection data, such as how much formic aldehyde is generated from which construction material and how much formic aldehyde is present in the room environment, can be obtained, easily.

In other embodiment of the formic aldehyde analyzing method, the analyzing kit is provided with:

(i) 2N-KOH solution (aqueous sodium hydroxide having a normality of 2) is employed as the collecting liquid 28. Ten to twenty impingers 14 respectively filled with 2.0 ml of this collecting liquid 28;

(ii) one Bial bottle A (having volume of 50 to 100 ml) containing AHMT reagent prepared by using $HClO_4$;

(iii) one Bial bottle B (having volume of 50 to 100 ml) containing $KIO_4$ reagent;

(iv) several plastic injectors (having volume of 1 ml);

(v) one impinger containing a standard color solution;

(vi) one sand glass (for 20 minutes); and (vii) one portable absorptiometer.

On the other hand, the concentrations of the AHMT reagent and $KIO_4$ reagent necessary for analysis are set so that optimal reacting condition with respect to the collecting liquid 28 can be obtained, and the liquid amount to be added by the injector can be small. Namely, the composition of AHMT reagent used is AHMT: 1% and $HClO_4$: 4 to 5%, and the composition of $KIO_4$ reagent used is $KIO_4$: 1% and KOH: 0.2 to 0.3 N.

The operation procedure for measuring formic aldehyde concentration by means of this analysis kit is the same as that of the former kit.

On the other hand, in the shown embodiment, concerning the collecting liquid 28 and the AHMT reagent, the following matters are considered. Since the AHMT reagent cannot be dissolved without adding acid, HCl is normally added thereto upon dissolving this reagent. Upon handling this reagent, the reagent is sampled by the injector as set forth above in order to improve operability. However, considering repeated sampling of the HCl-added AHMT reagent by the injector, corrosion should be caused on the injection needle because of HCl. Thus, the duration of the needle is considered to be quite short. Also, the reagent may be contaminated by eluted substance from the needle, such as iron ion generated by corrosion of the needle, which possibly causes error in analysis. Therefore, in the shown embodiment, for dissolving the AHMT reagent, $HClO_4$ is used in place of HCl. By this, corrosion of the injection needle and contamination of reagent can be avoided. On the other hand, 2N-KOH (potassium hydroxide solution having a normality of 2) may be employed as the collecting liquid 28 in addition to the foregoing 2N-NaOH. However, when $HClO_4$ is employed in AHMT reagent and when 2N-KOH is employed as the collecting liquid, potassium perchlorate, which is hardly water-soluble, is formed by reaction of $HClO_4$ and KOH when AHMT reagent is added to the collecting liquid 28, causing white turbidity in the sample solution. Therefore, considering that $HClO_4$ is used for AHMT reagent, 2N-NaOH is employed as the collecting liquid 28.

In either analyzing method, AHMT reagent is added to the collecting liquid 28 after gas collecting operation, and subsequently, $KIO_4$ reagent is added. An embodiment of an analyzing method of formic aldehyde which can further simplify the analyzing method will be discussed.

In this case, analyzing kit is provided with:

(i) ten to twenty impingers normally filled with 2 to 3 ml of the collecting liquid 28;

(ii) one impinger containing the standard color solution;

(iii) several plastic injectors (having volume of 1 ml); and (iv) one portable absorptiometer.

Particularly, the shown embodiment is designed to eliminate the operation for adding reagents after completing the collection, and waiting time of the reaction process. Therefore, in the shown embodiment, the collecting liquid 28 is prepared by mixing an alkali reagent and a reducing reagent, such as sodium hyposulfite and so forth, at an appropriate mixing ratio. In the conventional method, three kinds of reagents, which are the alkali reagent, the AHMT reagent, and $KIO_4$ reagent are used separately. In this case, when these reagents are preliminarily mixed, normal reaction with formic aldehyde cannot be caused. Therefore, it becomes necessary to add them separately in the predetermined sequential order and by keeping time interval required for reaction.

In contrast, when the collecting agent 28 of the shown embodiment is employed, it becomes possible to add AHMT liquid to the collecting liquid 28 before gas collecting operation, and $KIO_4$ reagent becomes unnecessary.

Then, since the AHMT reagent can be added in advance, color indication reaction can be carried out along with gas collection, and gas collecting operation can be performed by visually monitoring the condition thereof. Since color indication reaction progresses in conjunction with gas collection, it becomes possible to omit the period of time for waiting for reaction by adding AHMT reagent after gas collection. Furthermore, $KIO_4$ reagent is required for generating a red colored substance by oxidizing the reactive intermediate product of AHMT reagent and formic aldehyde. Since AHMT reagent can be added in advance, oxygen in the air introduced into the collecting liquid 28 during the process of gas collection may serve as oxidation agent, in the place of $KIO_4$ reagent. As a result, $KIO_4$ reagent becomes unnecessary. Next, operation procedure in measurement of formic aldehyde concentration using this analyzing kit will be discussed hereinafter.

In this case, the procedure is quite simple:

(I) 0.5 ml of AHMT solution is added by the injector to the impinger 14 containing the collecting liquid 28, and gas is sucked. At this time, 3 liters of gas suction amount is taken as a standard, and about 10 minutes is taken as the reference necessary period of time.

(II) The indication value is read by setting the impinger 14 to the absorptiometer, and the read value is obtained as formic aldehyde concentration.

Namely, in the shown embodiment, a given amount of collecting liquid 28, prepared by mixing the alkali reagent and the reducing reagent, such as sodium hyposulfite and so forth, at an appropriate mixing ratio, is filled in the impinger 14. Then, the given amount of the air in the inspection objective space is passed through the impinger 14. In conjunction therewith, the standard color solution is set in the absorptiometer for adjustment, so that the indication value equals to the predetermined value. Then, the impinger 14 is set in the absorptiometer, and analysis is made by detecting formic aldehyde concentration from the indication value.

What is claimed is:

1. A gas collecting system comprising:

a portable air pump which is driven by a portable battery to suck a gas in an inspection objective space;

a collection vessel, in which a collecting liquid for collecting an inspection objective gas from said gas is filled;

an induction passage having one end connected to said collection vessel and the other end communicated with said inspection objective space for introducing said gas into said collection vessel;

a suction passage having one end connected to said collection vessel and the other end connected to a suction port of said air pump for introducing said gas in said collection vessel into said air pump;

an accumulation body connected to a discharge port of said air pump, accumulating said gas discharged from said air pump and serving as a volumeter;

drying means disposed between said accumulation body and said collection vessel for drying said gas;

a pressure switch detecting an internal pressure of said accumulation body;

a bypass passage connecting said accumulation body to said suction port of said air pump bypassing said collection vessel; and switching means for switching a flow path connecting said accumulation body to either one of said discharge port of said air pump and said bypass passage, and in conjunction therewith, connecting said discharge port of said air pump to an ambient air opening passage when said accumulation body is connected to said bypass passage.

2. A gas collecting system as set forth in claim 1, which includes a main receptacle box and an auxiliary receptacle box mounted on said main receptacle box, said main receptacle box receives said air pump and said battery therein and has mounting surfaces for mounting said drying means and said collection vessel, said auxiliary receptacle box receives said switching means and said pressure switch therein, and has a mounting portion for detachably mounting said accumulation body.

3. A gas collecting system as set forth in claim 1, wherein said accumulation body is a foldable and exchangeable bag.

4. A gas collecting system as set forth in claim 3, wherein said bag is a vinyl bag.

5. A gas collecting system as set forth in claim 1, wherein said collection vessel is formed with transparent material to be used as a color comparison tube, and is also used as a reaction tube to be filled with reagents reacting with said inspection objective gas.

6. A gas collecting system as set forth in claim 1, wherein said pressure switch detects an internal pressure of said accumulation body reaching a predetermined pressure to output a stop signal for said air pump.

7. A gas collecting system as set forth in claim 1, wherein said pressure switch is connected among said air pump, a buzzer and a power source supplying operation power to said air pump and said buzzer, said pressure switch being constructed with a bag-formed extending member communicated with said accumulation body and causing expanding and contracting deformation by a pressure of said gas introduced from said accumulation body, a cylindrical guide surrounding said extending member to guide said extending member in expanding direction, and a switch main body being provided in opposition to said extending member in expanding direction thereof and being depressed by said expanding member for selectively establishing connection between a common terminal and either one of two switching terminals, wherein, each of said switching terminals is connected to said buzzer and said air pump, respectively, and said common terminal is connected to said power source, and when an internal pressure of said accumulation body is reached to a predetermined pressure, the connection with said common terminal is switched from said switching terminal of said air pump to said switching terminal of said buzzer by said extending member expanded in response thereto.

8. A gas collecting system as set forth in claim 1, wherein at least one of said induction passage and said suction passage has a capillary portion.

9. A gas collecting system as set forth in claim 1, wherein said collection vessel is formed into a cylindrical shape and its opening portion is closed by a cap, and said induction passage and said suction passage have an injection needle form tube portion, respectively, these tube portions being inserted into said collection vessel through said cap.

10. A gas collecting system as set forth in claim 9, wherein at least a portion of said cap covering said opening portion of said collection vessel is coated with an insulation layer of a material not influencing said collecting liquid.

11. A gas collecting system as set forth in claim 9, wherein said injection needle form tube portion is closed at a tip end thereof and is formed with a laterally oriented communication opening in the vicinity of said tip end portion.

12. A gas collecting system as set forth in claim 1, wherein said switching means is connected to a speed adjusting switch controlling driving speed of said air pump by varying a supply voltage to said air pump from said battery in response to switching operation of said flow path, when said discharge port of said air pump is connected to said accumulation body, said air pump is driven at low speed, and when said bypass passage is connected to said accumulation body, said air pump is driven at high speed.

13. A gas collecting system as set forth in claim 1, wherein a check valve is provided on the upstream side of said suction port of said air pump to only allow said gas flow to said suction port.

14. A gas collecting system as set forth in claim 1, wherein a given amount of 2N-NaOH solution as said collecting liquid is filled in said collection vessel, after passing a given amount of said gas containing said inspection objective gas, a given amount of AHMT reagent prepared by using $HClO_4$ as said reagents is filled within said collection vessel to leave for a given period, and in conjunction with, an indication value is adjusted to a predetermined value by setting a standard color solution in an absorptiometer, then, a given amount of $KIO_4$ reagent as said reagents is added into said collection vessel, and then, said collection vessel is set in said absorptiometer for detecting concentration of formic aldehyde from the indication value thereof.

15. A gas collecting system as set forth in claim 1, wherein a given amount of 2N-KOH solution as said collecting liquid is filled in said collection vessel, after passing a given amount of said gas containing said inspection objective gas, a given amount of AHMT reagent as said reagents is filled within said collection vessel to leave for a given period, and in conjunction with, an indication value is adjusted to a predetermined value by setting a standard color solution in an absorptiometer, then, a given amount of $KIO_4$ reagent as said reagents is added into said collection vessel, and then said collection vessel is set in said absorptiometer for detecting concentration of formic aldehyde from the indication value thereof.

16. A gas collecting system comprising:
- a portable air pump which is driven by a portable battery to suck a gas in an inspection objective space;
- a collection vessel, in which a collecting liquid for collecting an inspection objective gas from said gas is filled;
- an induction passage having one end connected to said collection vessel and the other end communicated with said inspection objective space for introducing said gas into said collection vessel;
- a suction passage having one end connected to said collection vessel and the other end connected to a suction port of said air pump for introducing said gas in said collection vessel into said air pump;
- an accumulation body connected to a discharge port of said air pump, accumulating said gas discharged from said air pump and serving as a volumeter;
- drying means disposed between said accumulation body and said collection vessel for drying said gas;
- a pressure switch detecting an internal pressure of said accumulation body;
- a bypass passage connecting said accumulation body to said suction port of said air pump bypassing said collection vessel;
- switching means for switching a flow path connecting said accumulation body to either one of said discharge port of said air pump and said bypass passage, and in conjunction therewith, connecting said discharge port of said air pump to an ambient air opening passage when said accumulation body is connected to said bypass passage;
- a main receptacle box receiving said air pump and said battery therein and having mounting surfaces for mounting said drying means and said collection vessel; and
- an auxiliary receptacle box mounted on said main receptacle box, receiving said switching means and said pressure switch therein, and having a mounting portion for detachably mounting said accumulation body, wherein,
  - said collection vessel is formed of a transparent material to be used as a color comparison tube, and is also used as a reaction tube filled with reagents reacting with said inspection objective gas,
  - said pressure switch detects an internal pressure of said accumulation body reaching a predetermined pressure for outputting a stop signal of said air pump, and said accumulation body is a foldable and exchangeable bag.

17. A gas collecting system as set forth in claim 1, which further comprises:
- a casing covering said inspection objective space in a sealing condition from outside to enclose said inspection objective gas discharged from an inspection object enclosed therein;
- a sampling port provided with said casing, and connected to said induction passage for introducing said gas containing said inspection objective gas in said casing into said collection vessel;
- a supply port provided with said casing for supplying a reference gas into said casing depending upon suction of said gas in said casing by said air pump, and
- a capillary passage disposed between said sampling port and said accumulation body for lowering flow velocity of said gas sucked.

18. A gas collecting system as set forth in claim 17, wherein said casing has an opening in a bottom portion where a packing fitting said casing with said inspection object in gas-tight fashion is provided.

19. A gas collecting system as set forth in claim 17, wherein said casing is a chamber receiving a material piece to be inspected as said inspection object.

20. A gas collecting system as set forth in claim 17, wherein said casing is formed of a transparent material.

21. A gas collecting system as set forth in claim 17, wherein said capillary passage is disposed between said sampling port and said collection vessel.

22. A gas collecting system as set forth in claim 17, wherein a filter is connected to said supply port, and said reference gas is an ambient air purified by said filter.

23. A gas collecting system as set forth in claim 17, wherein a reference gas receptacle body filled with said reference gas is connected to said supply port, and said reference gas is supplied to said casing from said reference gas receptacle body.

24. A gas collecting system as set forth in claim 17, a stirring means is provided in said casing to stir said gas therein.

25. A gas collecting system comprising:
- a casing covering an inspection objective space in a sealing condition from outside to enclose an inspection objective gas discharged from an inspection object enclosed therein;
- a sampling port provided with said casing to sample a gas containing said inspection objective gas in said casing;
- an air pump sucking said gas from said inspection objective space in said casing;
- a supply port provided with said casing for supplying a reference gas into said casing depending upon suction of said gas in said casing by said air pump;
- a collection vessel, in which a collection liquid for collecting said inspection objective gas from said gas is filled;
- an induction passage having one end connected to said collection vessel and the other end connected to said sampling port for introducing said gas into said collection vessel;
- a suction passage having one end connected to said collection vessel and the other end connected to a suction port of said air pump for introducing said gas in said collection vessel into said air pump;
- an accumulation body connected to a discharge port of said air pump, accumulating said gas discharged from said air pump and serving as a volumeter;
- a capillary passage disposed between said sampling port and said accumulation body for lowering flow velocity of said gas sucked;
- drying means disposed between said accumulation body and said collection vessel for drying said gas;
- a pressure switch detecting an internal pressure of said accumulation body;
- a bypass passage connecting said accumulation body to said suction port of said air pump bypassing said collection vessel; and
- switching means for switching a flow path connecting said accumulation body to either one of said discharge port of said air pump and said bypass passage, and in conjunction therewith, connecting said discharge port of said air pump to an ambient air opening passage when said accumulation body is connected to said bypass passage, wherein, said casing has an opening in a bottom portion, on which a packing for fitting said casing with said inspection object in gas-tight fashion is provided, a filter is connected to said supply port, and said reference gas is an ambient air purified by said filter.

26. A gas collecting system as set forth in claim 1, which further comprises:

a casing covering said inspection objective space in a sealing condition from outside to enclose said inspection objective gas discharged from an inspection object enclosed therein;

a sampling port provided with said casing, and connected to said induction passage for introducing said gas containing said inspection objective gas in said casing into said collection vessel;

an internal pressure maintaining bag provided in said casing and having expandability and sealing ability; and a pressure induction passage connected to said internal pressure maintaining bag through said casing and introducing a pressure adjusting gas for expanding said internal pressure maintaining bag according to lowering of the internal pressure of said casing.

27. A gas collecting system as set forth in claim 26, wherein said casing has an opening in a bottom portion, and a packing for fitting said casing with said inspection object in gas-tight fashion is provided on said opening.

28. A gas collecting system as set forth in claim 26, wherein said casing is a chamber receiving a material piece to be inspected as said inspection object.

29. A gas collecting system as set forth in claim 26, wherein said casing is formed of a transparent material.

30. A gas collecting system as set forth in claim 26, a stirring means is provided in said casing and said stirring means stirs said gas in said casing.

31. A gas collecting system as set forth in claim 26, wherein said pressure adjusting gas is introduced through said pressure induction passage into said internal pressure maintaining bag by a pressure reduction in said casing.

32. A gas collecting system as set forth in claim 26, wherein a port opening and closing means is disposed between said sampling port and said induction passage for opening and closing therebetween, and a pressure introducing means for opening and closing said pressure introducing passage is provided therewith.

33. A gas collecting system as set forth in claim 26, which further comprises:

a volume varying bag provided in said casing and having expandability and sealing ability, and a gas supplying and discharging passage connected to said volume varying bag through said casing, for supplying and discharging a volume adjusting gas to said volume varying bag to vary volume in said casing by expanding and deflating said volume varying bag.

34. A gas collecting system as set forth in claim 33, wherein at least either one of said internal pressure maintaining bag and said volume varying bag is disposed in plural in said casing.

35. A gas collecting system as set forth in claim 33, wherein an opening and closing means for said gas supplying and discharging passage is provided therewith.

36. A gas collecting system as set forth in claim 33, wherein an adjusting gas receptacle body filled with said pressure adjusting gas or said volume adjusting gas is connected to at least either one of said pressure induction passage and said gas supplying and discharging passage, and these gas are supplied from said adjusting gas receptacle body.

37. A gas collecting system comprising:

a casing covering an inspection objective space in a sealing condition from outside to enclose an inspection objective gas discharged from an inspection object enclosed therein;

a sampling port provided with said casing to sample a gas containing said inspection objective gas in said casing;

an air pump sucking said gas from said inspection objective space in said casing;

a collection vessel filled with a collecting liquid for collecting said inspection objective gas from said gas;

an induction passage having one end connected to said collection vessel and the other end connected to said sampling port for introducing said gas into said collection vessel;

a suction passage having one end connected to said collection vessel and the other end connected to a suction port of said air pump for introducing said gas in said collection vessel into said air pump;

an accumulation body connected to a discharge port of said air pump, accumulating said gas discharged from said air pump and serving as a volumeter;

drying means disposed between said accumulation body and said collection vessel for drying said gas;

a pressure switch detecting an internal pressure of said accumulation body;

a bypass passage connecting said accumulation body to said suction port of said air pump bypassing said collection vessel;

switching means for switching a flow path connecting said accumulation body to either one of said discharge port of said air pump and said bypass passage, and in conjunction therewith, connecting said discharge port of said air pump to an ambient air opening passage when said accumulation body is connected to said bypass passage;

an internal pressure maintaining bag provided in said casing and having expandability and sealing ability;

a pressure induction passage connected to said internal pressure maintaining bag through said casing and introducing a pressure adjusting gas for expanding said internal pressure maintaining bag according to lowering of the internal pressure of said casing;

a volume varying bag provided in said casing and having expandability and sealing ability; and a gas supplying and discharging passage connected to said volume varying bag through said casing, for supplying and discharging a volume adjusting gas to said volume varying bag for varying volume in said casing by expanding and deflecting said volume varying bag.

38. A gas collecting system comprising:

a casing covering an inspection objective space in a sealing condition from outside to enclose an inspection objective gas discharged from an inspection object enclosed therein;

a pair of gas circulating ports provided with said casing and circulating a gas through said casing;

an air pump sucking said gas containing said inspection objective gas from said inspection objective space in said casing;

a collection vessel, in which a collection liquid collecting said inspection objective gas from said gas is filled;

an induction passage having one end connected to said collection vessel and the other end connected to one of said gas circulating ports of said casing for introducing said gas into said collection vessel;

a suction passage having one end connected to said collection vessel and the other end connected to a suction port of said air pump for introducing said gas in said collection vessel into said air pump;

a buffer disposed between a discharge port of said air pump and the other of said gas circulating ports of said casing to buffer a gas pressure by temporarily storing said gas discharged from said air pump, and in conjunction therewith, to circulate said gas to said casing again; and humidity adjusting means disposed between said buffer and said collection vessel for adjusting a humidity of said gas circulated to be constant.

39. A gas collecting system as set forth in claim 38, wherein said casing has an opening in a bottom portion, and a packing for fitting said casing with said inspection object in gas-tight fashion is provided on said opening.

40. A gas collecting system as set forth in claim 38, wherein said casing is a chamber receiving a material piece to be inspected as said inspection object.

41. A gas collecting system as set forth in claim 38, wherein said casing is formed of a transparent material.

42. A gas collecting system as set forth in claim 38, wherein said buffer is a bag to be expanded and deflected depending upon a difference between a pressure of said gas stored therein and an ambient air pressure.

43. A gas collecting system as set forth in claim 38, wherein said humidity adjusting means is a container filled with a humidity adjusting liquid adjusting humidity of said gas.

44. A gas collecting system as set forth in claim 43, wherein said humidity adjusting liquid is a salt solution.

45. A gas collecting system as set forth in claim 38, wherein said collection vessel is provided in plural and in parallel, and switching device disposed between said collection vessels and one of said gas circulating ports of said casing to selectively communicate said casing with either one of said collection vessels.

46. A gas collecting system as set forth in claim 45, wherein said switching device switches the communication between said respective collection vessels and said casing according to a lapsed time.

47. A gas collecting system as set forth in claim 46, wherein said switching device is controlled the switching operation by means of a timer.

48. A gas collecting system as set forth in claim 38, wherein said air pump is portable and is driven by a portable battery.

49. A gas collecting system as set forth in claim 38, wherein said collection vessel is formed with transparent material to be used as a color comparison tube, and is also used as a reaction tube to be filled with reagents reacting with said inspection objective gas.

50. A gas collecting system as set forth in claim 38, wherein said collection vessel is formed into a cylindrical shape and its opening portion is closed by a cap, and said induction passage and said suction passage having an injection needle form tube portion, respectively, these tube portions being inserted into said collection vessel through said cap.

51. A gas collecting system as set forth in claim 50, wherein said cap is coated with an insulation layer of a material not influencing said collecting liquid at least at a portion covering said opening portion of said collection vessel.

52. A gas collecting system as set forth in claim 38, wherein a given amount of 2N-NaOH solution as said collecting liquid is filled in said collection vessel, after passing a given amount of said gas containing said inspection objective gas, a given amount of AHMT reagent prepared by using $HClO_4$ as said reagents is filled within said collection vessel to leave for a given period, and in conjunction therewith, an indication value is adjusted to a predetermined value by setting a standard color solution in an absorptiometer, then, a given amount of $KIO_4$ reagent as said reagents is added into said collection vessel, and then, said collection vessel is set in said absorptiometer for detecting concentration of formic aldehyde from the indication value thereof.

53. A gas collecting system as set forth in claim 38, wherein a given amount of 2N-KOH solution as said collecting liquid is filled in said collection vessel, after passing a given amount of said gas containing said inspection objective gas, a given amount of AHMT reagent as said reagents is filled within said collection vessel to leave for a given period, and in conjunction with, an indication value is adjusted to a predetermined value by setting a standard color solution in an absorptiometer, then, a given amount of $KIO_4$ reagent as said reagents is added into said collection vessel, and then, said collection vessel is set in said absorptiometer for detecting concentration of formic aldehyde from the indication value thereof.

54. A gas collecting system comprising:

a casing covering an inspection objective space in a sealing condition from outside to enclose an inspection objective gas discharged from an inspection object enclosed therein;

a pair of gas circulating ports provided with said casing to circulate a gas through said casing;

an air pump sucking said gas containing said inspection objective gas from said inspection objective space in said casing;

a collection vessel filled with a collection liquid for collecting said inspection objective gas from said gas;

an induction passage having one end connected to said collection vessel and the other end connected to one of said gas circulating ports of said casing for introducing said gas into said collection vessel;

a suction passage having one end connected to said collection vessel and the other end connected to a suction port of said air pump for introducing said gas in said collection vessel into said air pump;

a buffer disposed between a discharge port of said air pump and the other of said gas circulating ports of said casing to buffer a gas pressure by temporarily storing said gas discharged from said air pump, and in conjunction therewith, to supply said gas to said casing again; and humidity adjusting means disposed between said buffer and said collection vessel for adjusting a humidity of said gas circulated to be constant, wherein said casing has an opening in a bottom portion, on which a packing for fitting said casing with said inspection object in gas-tight fashion is provided, said collection vessel is formed with transparent material to be used as a color comparison tube, and is also used as a reaction tube to be filled with reagents reacting with said inspection objective gas, said buffer is a bag to be expanded and deflected depending upon a difference between a pressure of said gas stored therein and an ambient air pressure, and said humidity adjusting means is a container filled with a humidity adjusting liquid prepared by a salt solution for adjusting humidity of said gas.

55. A gas collecting system comprising:

a casing covering an inspection objective space in a sealing condition from outside to enclose an inspection objective gas discharged from an inspection object enclosed therein;

a pair of gas circulating ports provided with said casing and circulating a gas through said casing;

an air pump sucking said gas containing said inspection objective gas from said inspection objective space in said casing;

a collection vessel filled with a collection liquid collecting said inspection objective gas from said gas;

an induction passage having one end connected to said collection vessel and the other end connected to one of said gas circulating ports of said casing for introducing said gas into said collection vessel;

a suction passage having one end connected to said collection vessel and the other end connected to a suction port of said air pump for introducing said gas in said collection vessel into said air pump;

a buffer disposed between a discharge port of said air pump and the other of said gas circulating ports of said casing to buffer a gas pressure by temporarily storing said gas discharged from said air pump, and in conjunction therewith, to circulate said gas to said casing again; and humidity adjusting means disposed between said buffer and said collection vessel for adjusting a humidity of said gas circulated to be constant, wherein said casing has an opening in a bottom portion, on which a packing for fitting said casing with said inspection object in gas-tight fashion is provided, said buffer is a bag to be expanded and deflected depending upon a difference between a pressure of said gas stored therein and an ambient air pressure, said humidity adjusting means is a container filled with a humidity adjusting liquid prepared by a salt solution for adjusting humidity of said gas, said collection vessel is provided in plural and in parallel, said collection vessels being formed with transparent material to be used as a color comparison tube, and being also used as a reaction tube to be filled with reagents reacting with said inspection objective gas, and switching device is disposed between said collection vessels and one of said gas circulating ports of said casing to selectively communicate said casing with either one of said collection vessels according to time counted.

* * * * *